US005714466A

United States Patent [19]
Sniderman et al.

[11] Patent Number: 5,714,466
[45] Date of Patent: Feb. 3, 1998

[54] METHOD OF USING ACYLATION STIMULATING PROTEIN

[75] Inventors: Allan D. Sniderman, Westmount; Katherine Cianflone, L'Acadie, both of Canada

[73] Assignee: McGill University, Montreal, Canada

[21] Appl. No.: 264,022

[22] Filed: Jun. 22, 1994

[30] Foreign Application Priority Data

Jun. 22, 1993 [GB] United Kingdom ............... 9312819

[51] Int. Cl.$^6$ ............... A61K 38/00; A61K 38/02; C07K 5/00; C07K 7/00
[52] U.S. Cl. ............... 514/12
[58] Field of Search ............... 514/12; 530/324, 530/300

[56] References Cited

PUBLICATIONS

Cianflone et al., *J. Biol. Chem.*, vol. 264, No. 1, issued Jan. 1989, pp. 426–430.
Sniderman et al., *Current Opinion in Lipidolegy*, vol. 3, pp. 202–207, 1992.
Hugli, *J. Biol Chem*, vol. 250, No. 21, pp. 8293–8301, Nov. 10, 1975.
Choy et al., *J. Biol. Chem.*, vol. 267, No. 18, pp. 12736–12741, Jun. 25, 1992.
Baldo et al., *J. Clin Invest.*, vol. 92, pp. 1543–1547, 1993 Sep.
Baldo et al., 1993, J. Clin. Invest. 92(3):1543–1557.
Bradford M., 1976, Anal. Biochem. 72:248–254.
Caporale et al., 1980, J. Biol. Chem. 255:10758–10763.
Chomczynski & Sacchi, 1987, Anal. Biochem. 162:156–159.
Choy et al., 1992, J. Biol. Chem. 267(18):12736–12741.
Cianflone et al., 1989, J. Biol. Chem. 264(1):426–430.
Cianflone et al., 1989, J. Lipid Res. 30(11):1727–1733.
Cianflone et al., 1990, J. Clin. Invest. 85(3):722–730.
Cianflone et al., 1992, Clin. Invest. Med. 15(2):132–140.
Cook et al., 1985, Proc. Natl. Acad. Sci. USA 82:6480–6484.
Cook et al., 1987, Science 237:402–405.
Flier et al., 1987, Science 237:405–408.
Germinaro et al., 1993, Metabolism 40(5):574–580.
Hauner et al, 1989, J. Clin. Invest. 84:1663–1670.
Hugli, T.E., 1975, J. Biol. Chem. 250:8293–8301.
Janatova et al., 1980, Biochem. 19:4471–4478.
Kandel et al, 1991, Cell 66:1095–1104.
Kwiterovich et al., 1990, Proc. Natl. Acad. Sci. USA 87:8980–8984.

Laemmli, U.K. 1970, Nature 227:680–685.
Lowe et al, 1990, Nucleic Acids Res. 18:1757–1761.
Neri & Frings, 1973, Clin. Chem. 19:1201–1202.
Pangburn, M. 1988, Methods in Enzymol. 162:639–653.
Sniderman et al., 1992, Curr. Opin. Lipidol. 3:202–207.
Schreiber et al., 1978, J. Exp. Med. 148:1722–1727.
Teng et al., 1983, Proc. Natl. Acad. Sci. USA. 80(21):6662–6666.
Teng et al., 1986, J. Clin. Invest. 77(3):663–672.
Teng et al., 1988, J. Physiol., Pharmacol. 66:239–242.
Toney et al., 1993, J. Biol. Chem. 268:1024–1031.
Van Harken et al., 1969, J. Biol. Chem. 244:2278–2285.
White et al., 1992, J. Biol. Chem. 267(13):9210–9213.
Yasruel et al., 1991, Lipids 26(7):495–499.

*Primary Examiner*—Avis M. Davenport
*Attorney, Agent, or Firm*—Klauber & Jackson

[57] ABSTRACT

The present invention relates to a method to determine the amount of ASP protein, a functional derivative or a functional fragment thereof in a plasma sample, wherein the ASP protein comprises the following amino acid sequence:

SEQ ID NO: 1

```
Ser Val Gln Leu Thr Glu Lys Arg Met Asx Lys Val Gly Lys Tyr Pro
1               5                   10                  15
Lys Glu Leu Arg Lys Cys Cys Glu Asp Gly Met Arg Glx Asn Pro Met
                20                  25                  30
Arg Phe Ser Cys Gln Arg Arg Thr Arg Phe Ile Ser Leu Gly Glu Ala
                35                  40                  45
Cys Lys Lys Val Phe Leu Asp Cys Cys Asn Tyr Ile Thr Glu Leu Arg
                50                  55                  60
Arg Gln His Ala Arg Ala Ser His Leu Gly Leu Ala
65                  70                  75
``` wherein the functional derivative comprises at least one selected from the group consisting of one or more amino acid substitution, one or more amino acid deletion and one or more amino acid addition with the proviso that the functional derivative has a biological activity functionally equivalent to ASP, and the functional fragment comprises part of the ASP amino acid sequence and has a biological activity functionally equivalent to ASP; the method comprises the steps of: a) eluting the plasma sample on a column; b) measuring the amount of the ASP protein, functional derivative or functional fragment thereof present in said sample by an immunoassay with antibodies specific against one or more sites on C3a. The present invention also relates to the use of any antagonist of the ASP protein, functional derivative or functional fragment thereof for the inhibition of triglyceride synthesis in a patient, wherein the antagonist is selected from the group consisting of inhibitors of the alternate complement pathway.

4 Claims, 13 Drawing Sheets

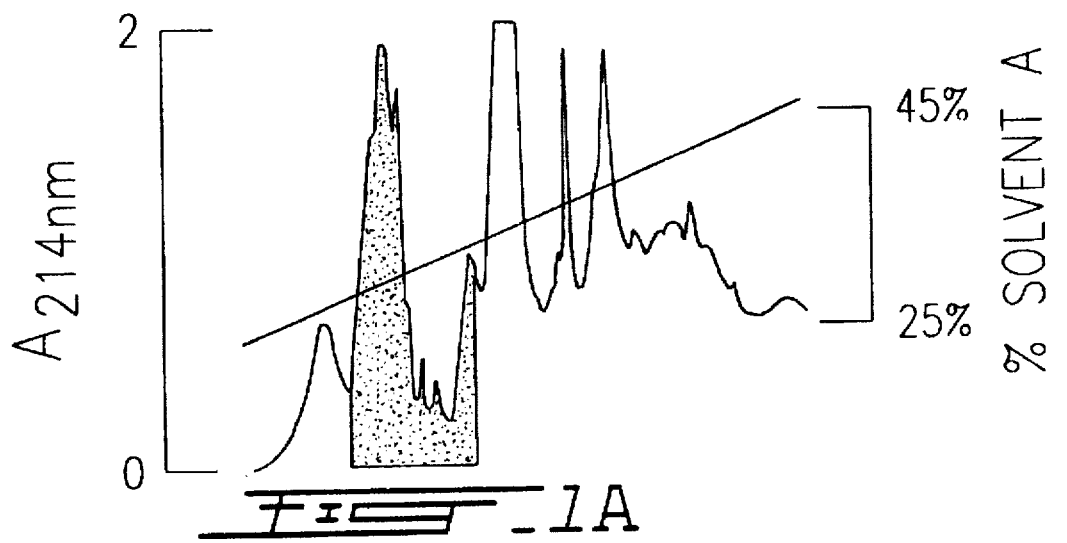
FIG._1A
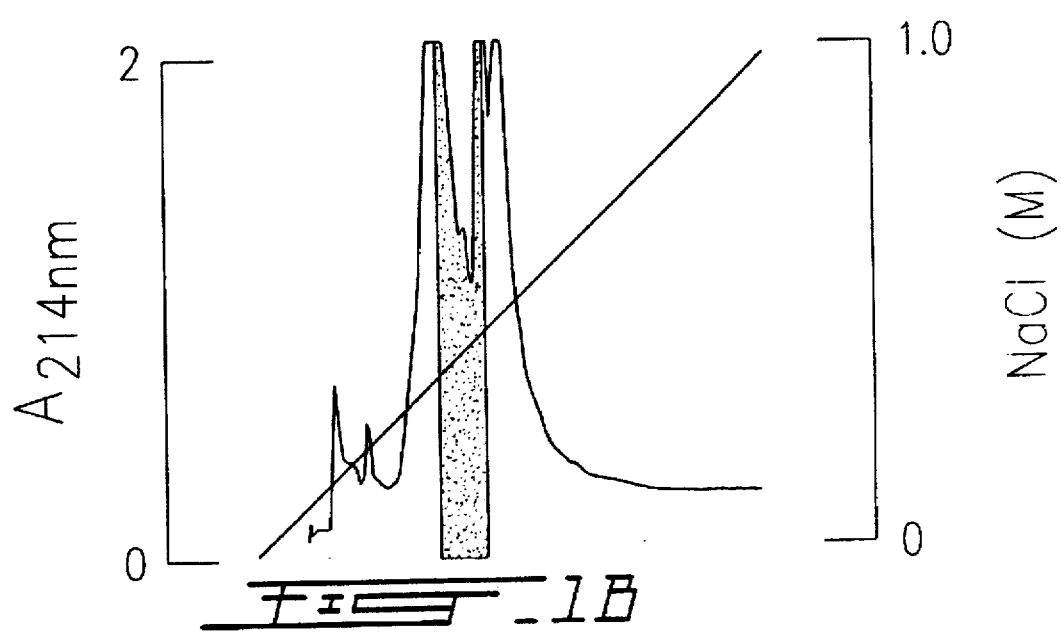
FIG._1B
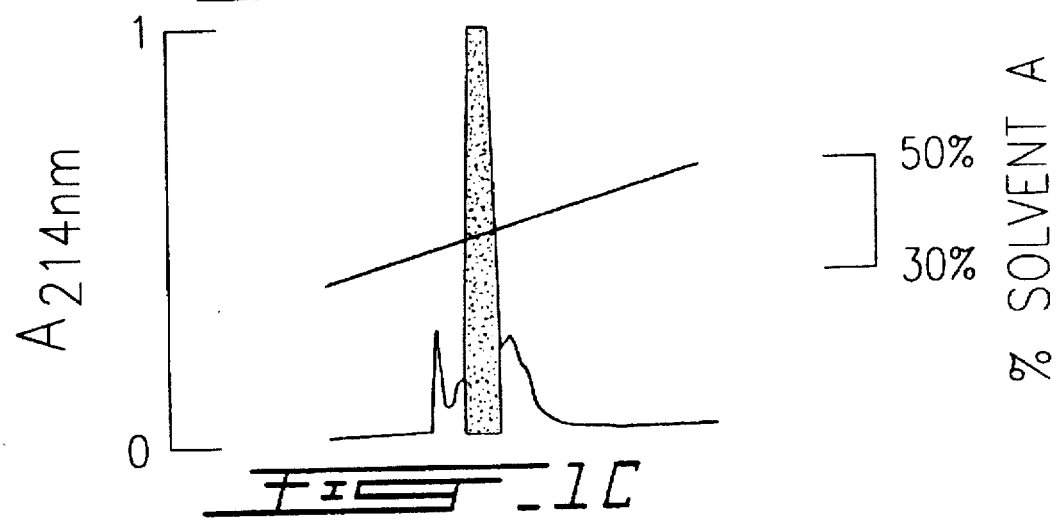
FIG._1C

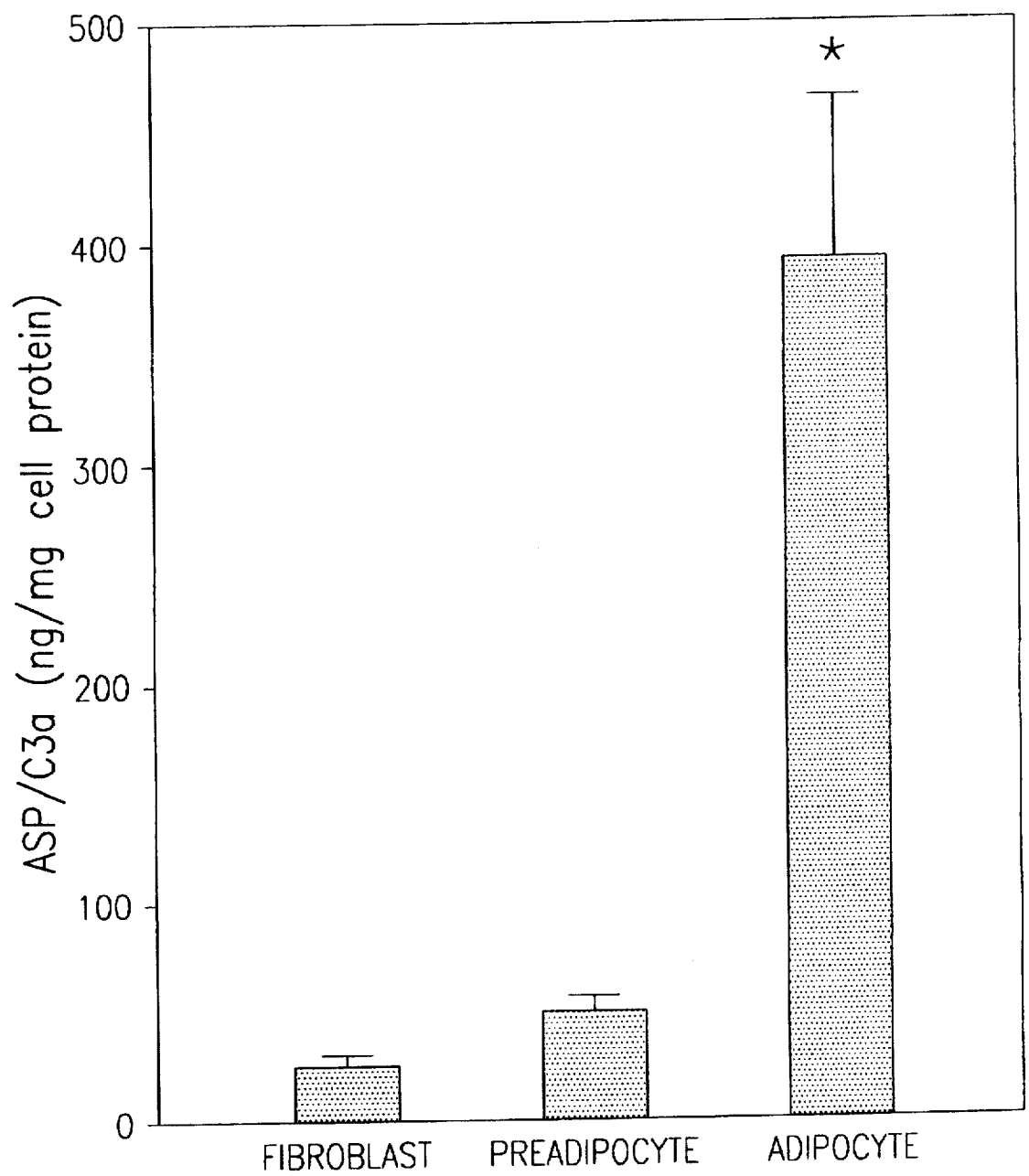
FIG_8

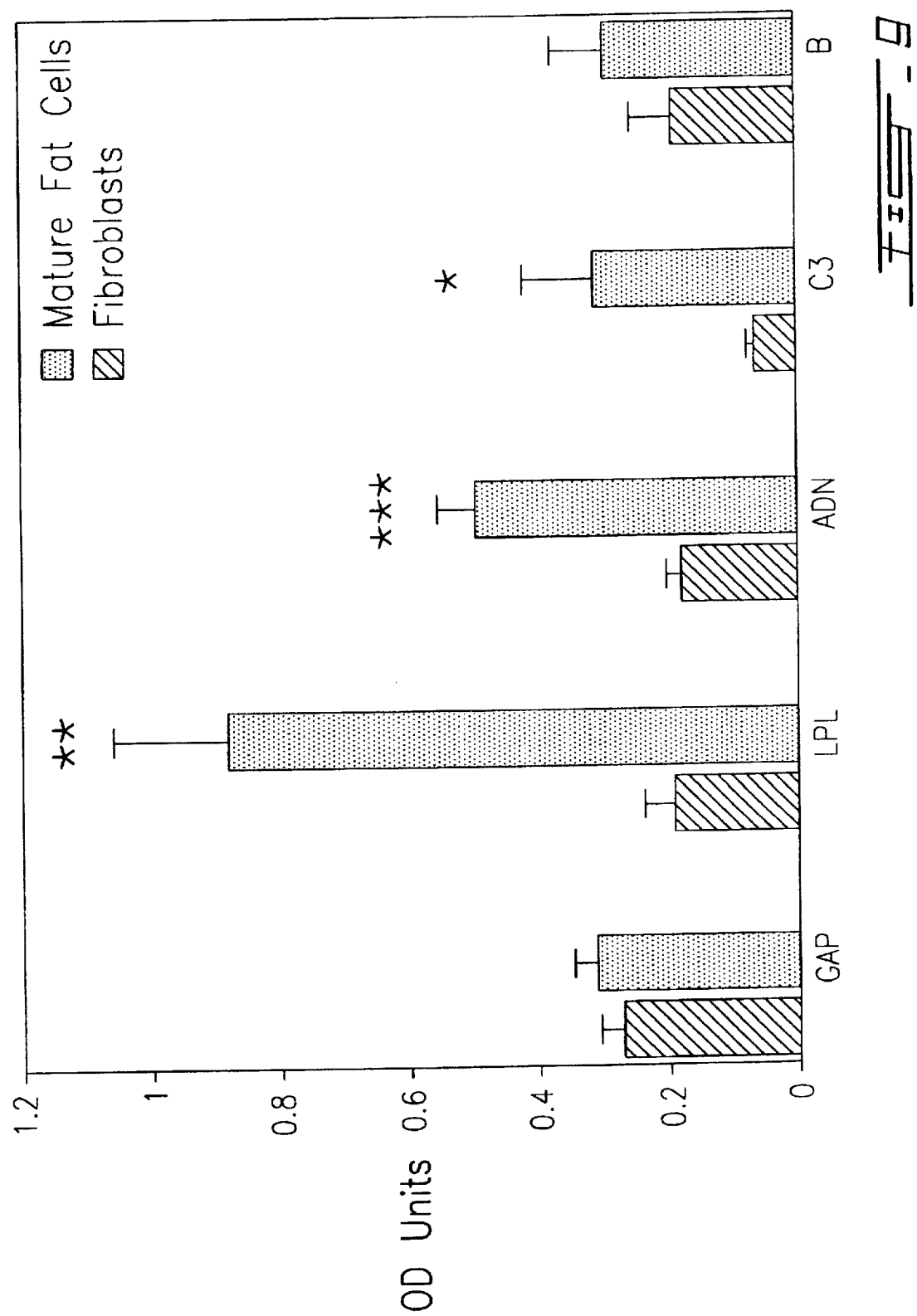

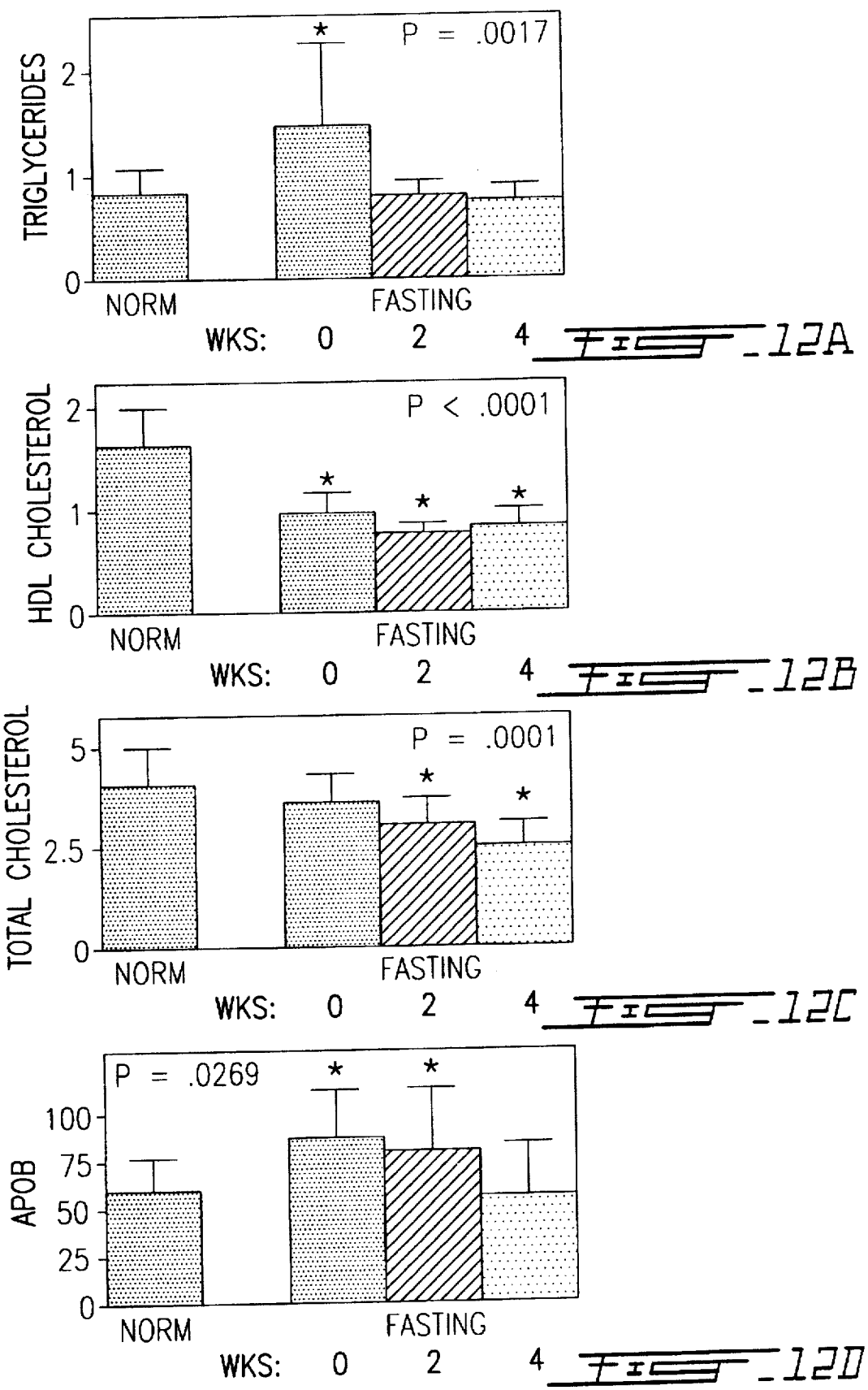

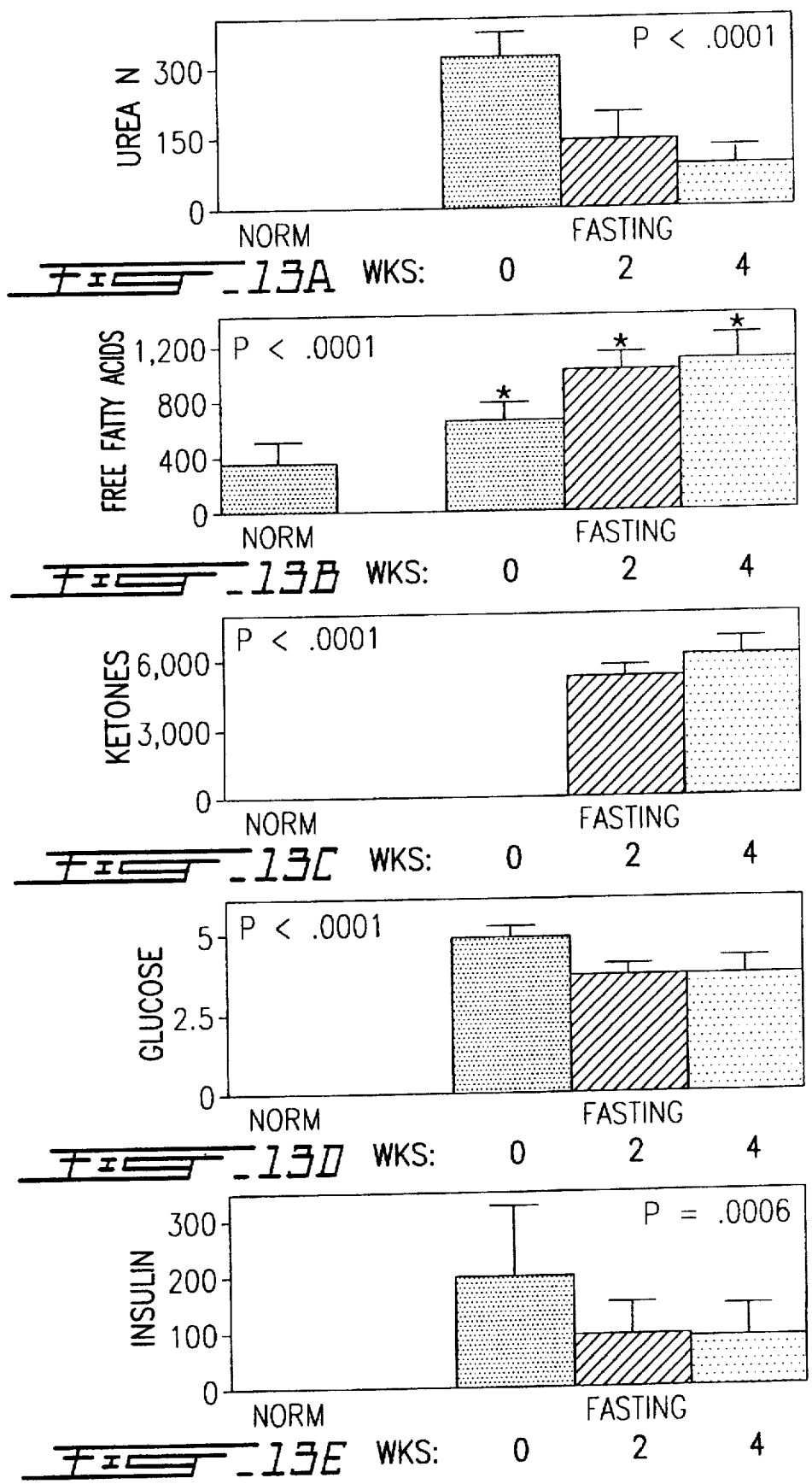

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 76 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

```
Ser Val Gln Leu Thr Glu Lys Arg Met Asx Lys Val Gly Lys Tyr Pro
 1               5                  10                  15
Lys Glu Leu Arg Lys Cys Cys Glu Asp Gly Met Arg Glx Asn Pro Met
            20                  25                  30
Arg Phe Ser Cys Gln Arg Arg Thr Arg Phe Ile Ser Leu Gly Glu Ala
        35                  40                  45
Cys Lys Lys Val Phe Leu Asp Cys Cys Asn Tyr Ile Thr Glu Leu Arg
    50                  55                  60
Arg Gln His Ala Arg Ala Ser His Leu Gly Leu Ala
65                  70                  75
```

METHOD OF USING ACYLATION STIMULATING PROTEIN

BACKGROUND OF THE INVENTION

1. Field of the Invention

The invention relates to an ASP protein involved in the triglyceride synthesis and its uses.

2. Description of Prior Art

In the course of studies to determine the metabolic defect in patients with HyperapoB (Teng et al., 1983, proc. Natl. Acad. Sci. USA. 80(21):6662-6666), it was observed that adipocytes from affected individuals synthesized triglycerides less rapidly than did adipocytes obtained from normals (Teng et al., 1988, J. Physiol., Pharmacol. 66:239-242). When triglyceride synthesis was measured in skin fibroblasts cultured from individuals in both groups, these differences were confirmed and shown to be due to a difference in response to a serum protein. Purification of the protein was undertaken and a single band on SDS gel electrophoresis obtained. The protein had an apparent molecular weight of 14 000, a pI of 9.0 and based on its in vitro activity was named Acylation Stimulating Protein (ASP) (Cianflone et al., 1989, J. Biol. Chem. 264(1):426-430).

Until recently, little was understood of the processes that control the rate at which human adipocytes make triglyceride. However, a metabolic pathway, the Adipsin-Acylation Stimulating Protein pathway has recently been described which appears to play a major role in regulating the rate at which this occurs (Baldo et al., 1993, J. Clin. Invest. 92(3):1543-1557). ASP is much more potent than insulin in stimulating the esterification of fatty acids into intracellular triglyceride in human fibroblasts and adipocytes (Cianflone et al., 1989, J. Biol. Chem. 264(1):426-430). The effector molecule of this pathway, acylation stimulating protein (ASP), is the most potent stimulant yet described of triglyceride synthesis in human adipocytes (Cianflone et al., 1989, J. Biol. Chem. 264(1):426-430). It achieves this effect by increasing the specific membrane transport of glucose (Germinaro et al., 1993, Metabolism 40(5):574-580) and the activity of the last enzyme involved in the synthesis of a triglyceride molecule, diacylglycerol acyltransferase (Yasruel et al., 1991, Lipids 26(7):495-499). Plasma ASP levels rise after an oral fat load, and the degree to which they do, relates directly to the rate at which triglycerides are cleared from plasma (Cianflone et al., 1989, J. Lipid Res. 30(11):1727-1733). On the other hand, a diminished response to ASP in patients with hyperapoB (Cianflone et al., 1990, J. Clin. Invest. 85(3):722-730; Kwiterovich et al., 1990, Proc. Natl. Acad. Sci. USA 87:8980-8984) is associated with increased hepatic VLDL production (Teng et al., 1986, J. Clin. Invest. 77(3):663-672), increased numbers of small dense LDL particles (Teng et al., 1983, Proc. Natl. Acad. Sci. USA. 80(21):6662-6666), and therefore, increased cardiovascular risk.

It would be highly desirable to be provided With the precise identity of ASP.

It would be highly desirable to be provided with a method to determine the amount of ASP protein in a plasma sample.

It would be highly desirable to be provided with the understanding of the regulation of triglyceride removal from plasma based on the adipsin-ASP pathway.

It would be highly desirable to be provided with the determination of the response of the adipsin-ASP pathway to a sustained fast with particular regard to the relation between the mobilization of energy from fatty acids and protein during this period.

SUMMARY OF THE INVENTION

One aim of the present invention is to provide evidence that ASP is, in fact, identical to a fragment of the third component of complement known as C3a-desArg. This finding when taken with the previous work of Spiegelman and his colleagues (Cook et al., 1987, Science 237:402-405; Flier et al., 1987, Science 237:405-408; Cook et al., 1985, Proc. Natl. Acad. Sci. USA 82:6480-6484; White et al., 1992, J. Biol. Chem. 267(13):9210-9213; Choy et al., 1992, J. Biol. Chem. 267(18):12736-12741) points to the presence of a novel system by which intracellular triglyceride synthesis may be regulated.

In accordance with the present invention there is provided a method to determine the amount of ASP protein, a functional derivative or a functional fragment thereof in a plasma sample, wherein said ASP protein comprises the following amino acid sequence

SEQ ID NO: 1

Ser Val Gln Leu Thr Glu Lys Arg Met Asx Lys Val Gly Lys Tyr Pro
1               5                   10                  15
Lys Glu Leu Arg Lys Cys Cys Glu Asp Gly Met Arg Glx Asn Pro Met
            20                  25                  30
Arg Phe Ser Cys Gln Arg Arg Thr Arg Phe Ile Ser Leu Gly Glu Ala
            35                  40              45
Cys Lys Lys Val Phe Leu Asp Cys Cys Asn Tyr Ile Thr Glu Leu Arg
        50                  55              60
Arg Gln His Ala Arg Ala Ser His Leu Gly Leu Ala
65                  70              75 wherein said functional derivative comprises at least one selected from the group consisting of one or more amino acid substitution, one or more amino acid deletion and one or more amino acid addition with the proviso that said functional derivative has a biological activity functionally equivalent to ASP, said functional fragment comprises part of the ASP amino acid sequence and has a biological activity functionally equivalent to ASP, said method comprises the steps of (a) eluting said plasma sample on a column; (b) measuring the amount of ASP protein, a functional derivative or a functional fragment thereof present in said sample by an immunoassay with antibodies specific against one or more sites on C3a.

In accordance with the present invention there is also provided for a use of any antagonist or agonist of ASP protein, a functional derivative or a functional fragment thereof for the inhibition of triglyceride synthesis in a patient, wherein said ASP protein comprises the following amino acid sequence

SEQ ID NO: 1

Ser Val Gln Leu Thr Glu Lys Arg Met Asx Lys Val Gly Lys Tyr Pro
1               5                   10                  15
Lys Glu Leu Arg Lys Cys Cys Glu Asp Gly Met Arg Glx Asn Pro Met
            20                  25                  30
Arg Phe Ser Cys Gln Arg Arg Thr Arg Phe Ile Ser Leu Gly Glu Ala
            35                  40              45
Cys Lys Lys Val Phe Leu Asp Cys Cys Asn Tyr Ile Thr Glu Leu Arg
        50                  55              60
Arg Gln His Ala Arg Ala Ser His Leu Gly Leu Ala
65                  70              75 wherein said functional derivative comprises at least one selected from the group consisting of one or more amino acid substitution, one or more amino acid deletion and one or more amino acid addition with the proviso that said functional derivative has a biological activity functionally equivalent to ASP, said functional fragment comprises part of the ASP amino acid sequence and has a biological activity functionally equivalent to ASP, and said antagonist is selected from the group consisting of inhibitors or stimulators of the alternate complement pathway. This inhibition or stimulation of triglyceride synthesis in a patient may be used for the treatment of obesity or of diabetes mellitus or related disorders by virtue of its stimulatory or inhibitory effect on cell glucose transport and increased fatty acid removal rate from plasma.

BRIEF DESCRIPTION OF THE DRAWINGS

FIG. 1(A–C) is a graph of protein elution at 214 nm for fraction (A) resolved by reverse phase on Vydac™ Protein C4, (B) by cation exchange on Mono-S HR 5/5™ and (C) by reverse phase on μBondapak™ C18;

FIG. 8 shows the ASP secretion by human skin fibroblasts, preadipocytes and differentiating adipocytes;

FIG. 9 shows the PCR amplification of human skin fibroblast and mature fat cell RNA;

FIG. 12(A–D) shows the sequential changes in plasma insulin, glucose, urine urea nitrogen, plasma free fatty acids and ketones compared to values in the control group;

FIG. 13(A–E) shows the sequential changes in body mass index (BMI) and plasma ASP in the obese group compared to values in the control group.

DETAILED DESCRIPTION OF THE INVENTION

Material

Figure 2:
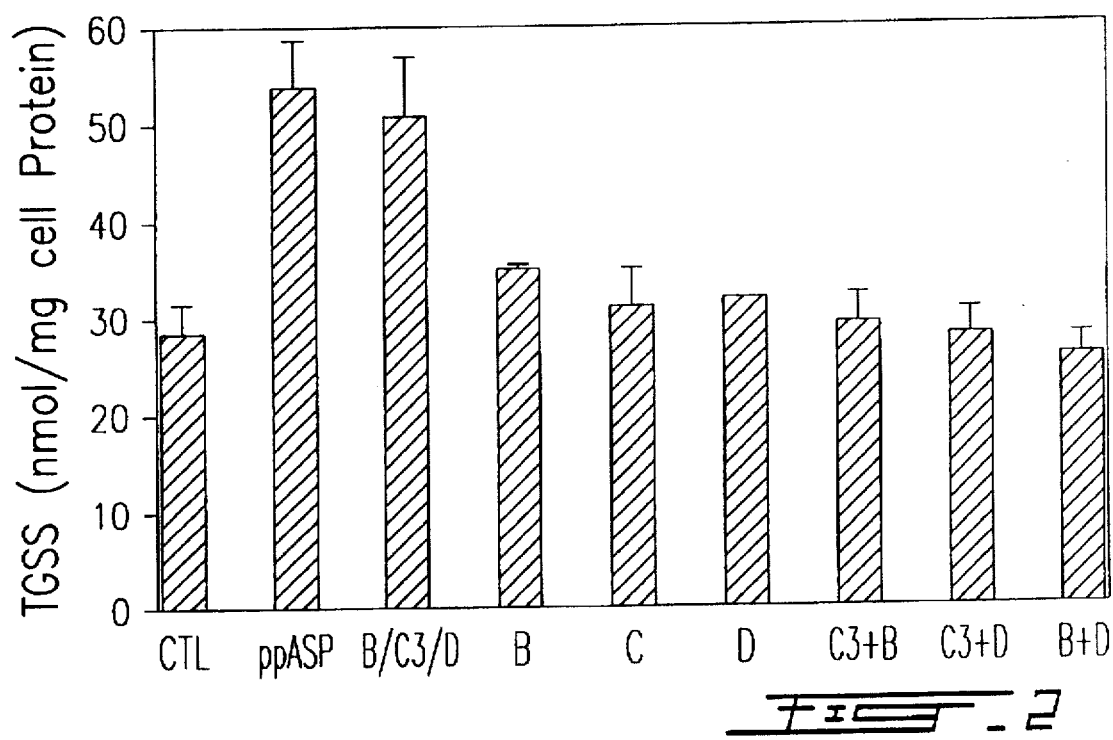
FIG. 2 is a graph of the biologic activity of in vitro generated C3a in nmol triglyceride synthesized per mg cell protein.

S-Sepharose Fast Flow™, Sephadex™ G-75, Mono-S™ HR 5/5 and columns used for standard chromatography and were obtained from Pharmacia (Uppsala, Sweden). μBondapak™ C18 reverse phase column was obtained from Waters (Millford, Mass.) and Vydac™ Protein C4 was obtained from the Separations group (Hesperia, Calif.). Trifluoroacetic acid (TFA) was obtained from Chromatographic Specialties Inc. (Brockville, Canada). HPLC grade acetonitrile (ACN), hexanes, ethyl ether and acetic acid were obtained from Fisher Scientific (Montreal, Canada). [9,10-$^3$H(N)]-Oleic acid (10.0 Ci/mmol) was obtained from Dupont-New England Nuclear (Mississauga, Canada). Oleic acid (sodium salt) and bovine serum albumin-essentially fatty acid free (BSA) were purchased from Sigma (St. Louis, Mo.). Human factor D, B and complement C3 were purchased from Calbiochem (San Diego, Calif.). Dulbecco's minimum essential medium/F12 (D-MEM/F12), Dulbecco's-phosphate buffered saline (D-PBS) and all other tissue culture supplies were obtained from Gibco (Burlington, Canada). Aqueous samples were concentrated with a stirred cell concentrator equipped with a YM-3 membrane from Amicon (Beverly, Mass.). Organic samples were evaporated in a centrifugal vacuum concentrator by Jouan (Canberra-Packard, Canada).

Purification ASP From Human Plasma

ASP was purified from human plasma in five sequential chromatographic steps that were performed in the following order: Cation exchange on S-Sepharose™ Fast Flow, gel filtration on Sephadex™ G-75, reverse phase on a semi-preparative Vydac™ Protein C4 (1.0×25 cm), cation exchange on Mono-S HR 5/5™ and reverse phase on μBondapak™ C18 (3.9×300 mm). For each chromatographic step, the activity of the column fractions were tested for their ability to stimulate triglyceride synthesis in cultured human skin fibroblasts. The S-Sepharose™ and Sephadex™ G-75 steps were performed as previously described (Cianflone et al., 1990, J. Clin. Invest. 85(3):722–730). The active fractions from S-Sepharose™, which correspond to the second half of the elution peak monitored by absorbance at 280 nm, were pooled (fraction A, 99±30 mg of protein, 274±60 ml, n=8), concentrated and fractionated on G-75. Those tubes with activity were pooled and concentrated to yield fraction B (7.4±3.4 mg of protein, 13±1.6 ml, n=8) and stored at −80° C.

Vydac™ Protein C4

Prior to reverse phase chromatography several batches of Fraction B were prepared and pooled (10–50 mg total). The pooled material was loaded on a Vydac™ Protein C4 column which was eluded with a linear gradient of 25%–65% solvent A (80% ACN) containing 0.1% TFA throughout over 60 minutes at a flow rate of 3 ml/minute and collected as 1 minute fractions with protein elution monitored at 214 nm. The biologic activity eluted from this column between 37% to 42% solvent A (fraction C) and the pool was stored at −80° C.

Mono-S™ HR 5/5

Fraction C from the Vydac™ C4 was loaded directly on a Mono-S™ HR 5/5 FPLC column equilibrated in solvent B (10 mM Tris, 10 mM NaCl, pH:7.1, sterile) and eluted from the Mono-S™ column with a 35 minute linear 0 to 1 M NaCl gradient in solvent B at a flow of 1 ml/minute and fractionated as 0.5 minutes/tube. Protein elution was monitored at 214 nm and activity for each fraction tested. The activity which eluted from this column between 280 to 400 mM NaCl (fraction D) was pooled and stored at −80° C.

μBondapak™ C18

A Waters UBondapak™ C18 column was used as a final purification step and was run using the same solvent system as for the Vydac™ Protein C4 column. After loading Fraction D on the column, bound proteins were eluted over 60 minutes with a linear gradient from 0% to 60% solvent A at a flow rate of 1 ml/minute and collected as 1 minute fractions. The biologic activity was found to elute at 38% solvent A (fraction. E).

Amino Acid Analysis and Protein Quantification

Amino acid hydrolysis was used for characterization of the final purified material. Samples were hydrolyzed in 6N HCl vapor in vacuo at 150° C. for 2 hours using a Pico-Tag™ work station and analyzed for amino acid composition on a Beckman™ model 6300A autoanalyser.

Ion Spray Ionization Mass Spectroscopy

Ion Spray mass spectra of ASP were obtained using an API III™ triple stage mass spectrometer with ion spray interface (SCIEX, Thornhill, Ontario, Canada) located at the National research Council of Canada, the Montreal Biotechnology Research Institute (Toney et al., 1993, J. Biol. Chem. 268:1024–1031).

Edman Sequencing

The N-terminal amino acid sequence of ASP was determined by subjecting the samples to gas-phase microsequencing on a Proton Instrument gas phase sequenator located at the Sheldon Biotechnology Centre of McGill University.

Culture of human skin fibroblasts

Fibroblasts were obtained from forearm skin biopsies of normolipidemic subjects. Primary cultures were established from explants and maintained in MME with 10% fetal calf serum supplemented with penicillin/streptomycin (100 IU/ml). Fibroblasts were subcultured every 7–10 days with a split ratio of 1:2 following a 10 minute incubation with 0.25% trypsin in $Mg^{2+}$ and $Ca^{2+}$-free D-PBS to detach the cells from the flask. Cells were used for experiments between passages 5 and 15 plated out at a concentration of $1 \times 10^4$ cells/cm$^2$ in 24 well dishes in 1 ml medium. At or near confluency, the day prior to experimentation, cells were changed to serum-free D-MEM/F12.

Measurement of biologic activity

The ability of column fractions to stimulate triglyceride synthesis was determined in cultured human skin fibroblasts as described previously (Cianflone et al., 1990, J. Clin. Invest. 85(3):722–730). Aliquots of column fractions from reverse phase chromatography were dried in a centrifuge evaporator and reconstituted in D-PBS. Following an overnight preincubation in serum-free D-MEM/F12, the media of the cells was replaced with 400 µl/well of D-MEM/F12 supplemented with 125 µM [9,10-$^3$H(N)]-Oleic acid (average specific activity: 40±10 DPM/pmol, n=11) complexed to bovine serum albumin (Van Harken et al., 1969, J. Biol. Chem. 244:2278–2285) in a 5:1 molar ratio and 100 µl/well of the test fraction aliquot. At the end of the incubation period (usually 18 hours), the cells were washed three times with 1 ml ice cold D-PBS and extracted with two 1 ml volumes of heptane:isopropanol (3:2). The lipids in the organic extract were separated and quantified as described previously (Cianflone et al., 1989, J- Biol. Chem. 264(1):426–430). Soluble cell protein was dissolved in 0.1 N NaOH and measured by the method of Bradford (Bradford M., 1976, Anal. Biochem. 72:248–254) using a commercial kit (Bio-Rad, Calif.). Bovine serum albumin was used as protein standard. Each column fraction was assayed in duplicate or triplicate. Data is expressed as mean±standard deviation.

Biologic Activity of In Vitro Generated C3a

C3a was generated enzymatically in vitro by incubating 100 µg of C3 with 10 µg of factor D and 100 µg of factor B in 2 mM $MgCl_2$ as previously described (Janatova et al., 1980, Biochem. 19:4471–4478). The mixture as well as each individual component, C3, factor B and factor D were assayed for biologic activity as above. The presence of C3a in the mixture was confirmed and quantified using a commercial RIA kit specific for C3a-desArg (Amersham Oakville, Canada). SDS-PAGE was performed by the method of Laemmli (Laemmli, U.K. 1970, Nature 227:680–685) using precast 5% to 20% gradient gels (BioRad, Calif.).

Results

The purification of ASP is shown in FIG. 1. Fractionated plasma containing small basic proteins isolated by ion exchange and gel filtration as previously described by Cianflone et al. (1990, J. Clin. Invest. 85(3):722–730) was further purified on a reverse phase HPLC Vydac™ C4 column and bioactivity was measured as the capacity of each fraction to stimulate fatty acid esterification to form triglyceride in normal human skin fibroblasts. The column profile is shown in panel A (FIG. 1), and the activity eluted between 37% and 42% of solvent A. Overall, recovery of activity averaged 60%. The active fractions (as highlighted in panel A) were loaded onto an ion exchange Mono S™ column and fractionated with a salt gradient. Activity was recovered between 280 and 400 mM NaCl (Fig. 1, panel B). Finally, the active fraction of the Mono S™ column was chromatographed on a C18 column and the activity in each fraction monitored. The activity is indicated in the profile in FIG. 1 (panel C) and ASP constituted the active fraction isolated which eluted at 38% solvent A.

ASP was characterized by amino acid terminal sequencing. The first 10 amino terminal amino acids yielded a sequence that exactly matched the sequence previously published for a fragment of complement C3, complement C3a (NH$_2$-Ser-Val-Gln-Leu-Thr-Glu-Lys-Arg-Met-Asp) (Hugli, T. E., 1975, J. Biol. Chem. 250:8293–8301). No other sequence was present in the active material. CNBr treatment, which cleaves at methionine, followed by Edman degradation amino terminal sequencing did not reveal any unexpected sequences, that is, any sequences other than those that are predicted from cleavage of C3a. Moreover, as shown in Table I, ASP amino acid composition matches that of C3a very closely. Of interest, ASP purified from plasma contains 10 Arg as does C3a-desArg, whereas C3a itself contains 11. These results were confirmed when protein mass analysis was performed by ion spray ionization. This demonstrated that the mass of the protein was 8933±0.3 mass units, .a mass that corresponds not to C3a (9088.7) but to C3a-desArg (8932.5) (Hugli, T. E., 1975, J. Biol. Chem. 250:8293–8301).

Figure 3:
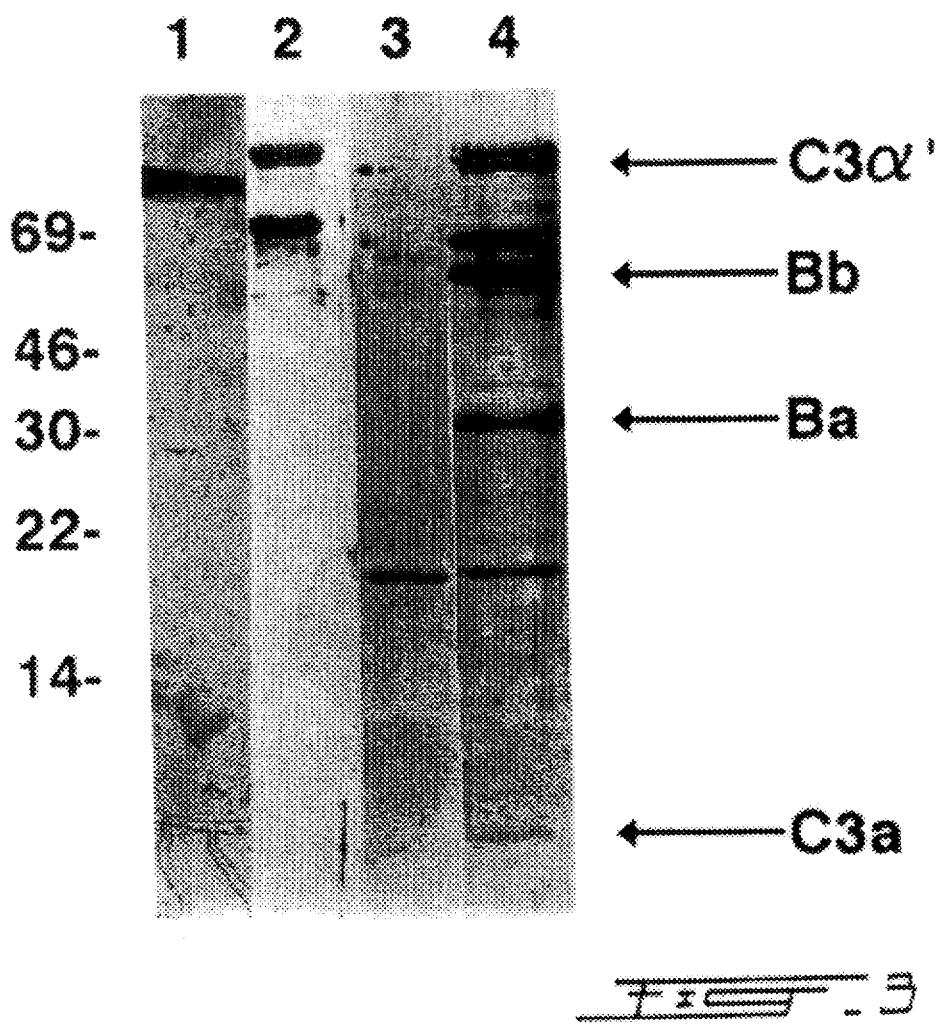
FIG. 3 is a gel electrophoresis of individual components B, C3 and D and in vitro generated C3a/ASP.

C3a is generated through the concerted actions of complement B, C3 and D (Schreiber et al., 1978, J. Exp. Med. 148:1722–1727). Therefore, purified complement C3, B and D were obtained and incubated together in 2 mM $MgCl_2$ under conditions reported to generated C3a in vitro (Janatova et al., 1980, Biochem. 19:4471–4478). This material was then tested for its ability to stimulate triglyceride synthesis in human skin fibroblasts. The results are shown in FIG. 2. The basal level of triglyceride synthesis in the fibroblasts was 29±3.3 nmol/mg cell protein. Addition of a partially purified preparation of ASP increased triglyceride synthesis to 55±6.6 nmol/mg cell protein, a 87% increase above basal. Addition of a mixture of B/C3/D resulted in a similar stimulation of triglyceride synthesis as seen with ASP. In contrast, addition of the individual components, complement C3, complement factor B and factor D did not increase triglyceride synthesis when added at the same concentrations as in the complete mixture. Moreover, addition of any two of the factors together: B+D, B+C3, C3+D also did not result in stimulation of triglyceride synthesis as shown in FIG. 2. That C3a/ASP is indeed generated when B, C3 and D are incubated together under appropriate conditions is shown in FIG. 3. Both factor B and faction D demonstrate single bands on SDS gel electrophoresis (Lanes 1 and 3) (Pangburn, M. 1988, Methods in Enzymol. 162:639–653). Complement C3 is composed of 2 chains, C3α (110 kD) and C3β (70 kD) attached by disulfide bridges that demonstrate two bands on gel electrophoresis (Lane 2) (Pangburn, M. 1988, Alternative pathway of complement, Methods in Enzymol. 162:639–653). Incubation of factors B, C3 and D produces several changes. Factor D enzymatically cleaves .factor B to generate Ba and Bb of molecular weights 30 kD and 60 kD, as indicated by arrows on FIG. 3

(lane 4). In addition, the binding of factor Bb to C3 will form the C3 convertase which generates C3α' (101 kD) and C3a (9 kD). All of the generated products of the reaction: C3α', Bb, Ba and C3a can be visualized on the gel as indicated by arrows.

Figure 4:
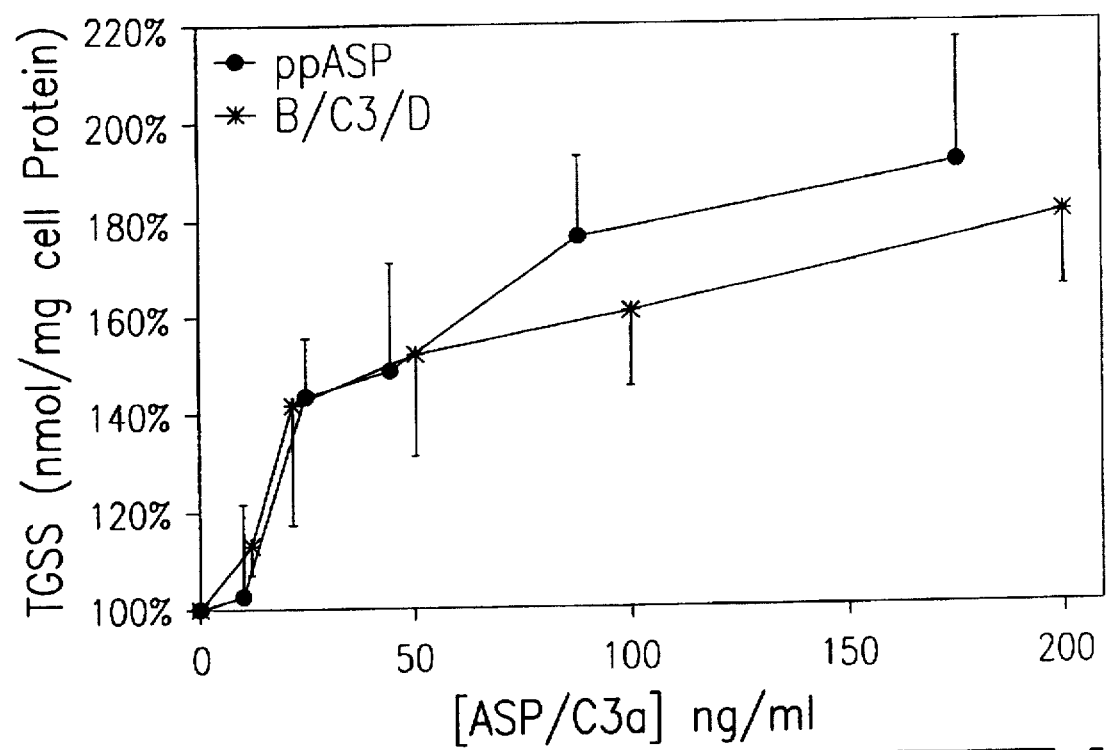
FIG. 4 is a graph of concentration dependent stimulation of triglyceride synthesis by in vitro generated C3a/ASP and serum ASP.

The capacity of in vitro generated C3a/ASP to stimulate triglyceride synthesis as compared to partially purifies plasma ASP is shown in FIG. 4. The amount of C3a mass present in both the purified complement component mixture and in the partially purified ASP derived from a small basic fraction of serum was measured by commercial radioimmunoassay (RIA). Increasing concentrations of ASP/C3a-desArg (as measured by RIA) were added to cells and triglyceride synthetic activity assessed. As shown in FIG. 4, the curves closely parallel each other. Therefore C3a generated in vitro is capable of stimulating triglyceride synthesis and the ASP triglyceride synthetic activity of the small basic partially purified serum fraction can be attributed principally to the C3a-desArg component.

The data presented indicate that ASP is identical in terms of amino acid composition, molecular mass and N-terminal amino sequence to a component of human complement, C3a-desArg. This result was not anticipated, and at first glance, appears physiologically implausible given that the precursor of C3a-desArg, C3a, is generally considered to be an anaphylotoxin generated through complement activation.

However, the studies of Speigelman and his colleagues indicate that components of complement may indeed play important roles in adipose tissue metabolism. They demonstrated that on differentiation murine 3T3 adipocytes express large amounts of a message for a protein which they named adipsin (adipocyte trypsin) which is secreted from such cells (Cook et al., 1987, Science 237:402–405). Plasma levels of adipsin and adipose tissue adipsin mRNA are both markedly suppressed in many, although not all, models of experimental obesity (Flier et al., 1987, Science 237:405–408). From this and other data, they concluded that adipsin might play a critical role in regulating the rate of lipolysis in adipocytes (Flier et al., 1987, Science 237:405–408).

The link to the complement pathway began with the demonstration that there was considerable homology between the mouse adipsin cDNA sequence and the corresponding amino acid sequence of human factor D, a protein integral to the activation of the alternate complement pathway (Cook et al., 1985, Proc. Natl. Acad. Sci. USA, 82:6480–6484). They then isolated a cDNA for human adipsin and showed that it encoded for a protein sharing 98% amino acid sequence identity with the protein sequence for purified human complement D (White et al., 1992, J. Biol. Chem. 267(13):9210–9213). Most recently, they demonstrated that under specific incubation conditions differentiated murine 3T3 adipocytes also synthesized and secreted the two other components involved in the initial steps of the alternate complement pathway, factor B and C3 and that C3a could be identified in the medium surrounding such cells (Choy et al., 1992, J. Biol. Chem. 267(18):12736–12741). Importantly, there was no evidence of complement C2 or C5 indicating that the distal steps of the complement pathway which lead to cell lysis were not operational (Choy et al., 1992, J. Biol. Chem. 267(18):12736–12741).

The present invention is focused on the regulation of triglyceride synthesis in human adipose tissue. ASP causes triglyceride synthesis to rise in fibroblasts and HepG2 cells but has a much more pronounced impact in differentiated adipocytes (Cianflone et al., 1989, J. Biol. Chem. 264(1): 426–430). Moreover, the data of the present invention and that of others indicates that the reduced rate of triglyceride synthesis in adipocytes from patients with HyperapoB might be due to reduced responsiveness to ASP, confirming the anabolic character of this protein (Teng et al., 1988, J. Physiol., Pharmacol. 66:239–242; Cianflone et al., 1990, J. Clin. Invest. 85(3):722–730; Kwiterovich et al., 1990, Proc. Natl. Acad. Sci. USA 87:8980–8984). The physicochemical data in accordance with the present invention indicate that ASP and C3a-desArg are identical. C3a-desArg is the product which results when the terminal arginine is cleaved from C3a, and given the large amounts of carboxypeptidase present in plasma, this would be the expected form in which C3a would be purified from this source. The present data establish that C3a-desArg is bioactive in so far as it can increase triglyceride synthesis. It is not known, however, to have immunocytologic or any other biologic activity (Caporale et al., 1980, J. Biol. Chem. 255:10758–10763).

A critical sector of experimental evidence in the present invention is derived from the experiments in which the precursor proteins, factors B, D (adipsin) and C3, were incubated under appropriate conditions to generate C3a and added to the medium bathing fibroblasts. The data indicate that triglyceride synthesis increased in direct proportion to the amount of C3a present. Moreover, the increase in triglyceride synthesis closely parallels that induced by addition of an equivalent amount of C3a-desArg present in a partially purified plasma preparation of ASP. Both lines of evidence, the purification of the active principal as C3a-desArg is the bioactive principle responsible for the increase in triglyceride synthesis.

Therefore, a conclusion different that of Spiegelman and colleagues is reached in accordance with the present invention. Although the Adipsin/ASP system is involved in the regulation of triglyceride metabolism in adipocytes, the data of the present invention indicate that the function of this system is to increase the rate of triglyceride synthesis in adipocytes rather than to increase the rate at which lipolysis occurs. If so, the decrease in adipsin mRNA reported in the obese mouse models would represent an adaptive rather than causal finding (Flier et al., 1987, Science 237:405–408). Adipocytes contain message levels for the three proteins necessary to generate ASP (Choy et al., 1992, J. Biol. Chem. 267(18):12736–12741). The data of the present invention point, therefore, to the possible existence of what would be a unique regulatory system in which the synthesis of a series of proteins then generates a product which by acting on the cell surface alters the essential metabolic property of the cell.

TABLE I

Amino acid composition
The amino acid composition of ASP determined as described above and was compared to published compositions of C3a and C3a-desArg (Laemmli, U.K. 1970, Nature 227:680–685).

| Amino Acid | ASP | C3a* | C3a-desArg* |
|---|---|---|---|
| Asx | 4.9 | 5 | 5 |
| Thr | 2.8 | 3 | 3 |
| Ser | 3.4 | 4 | 4 |
| Glx | 9.0 | 9 | 9 |
| Pro | 2.1 | 2 | 2 |
| Gly | 4.1 | 4 | 4 |
| Ala | 3.9 | 4 | 4 |
| Cys | 6.1 | 6 | 6 |
| Val | 3.5 | 3 | 3 |
| Met | 2.7 | 3 | 3 |
| Ile | 2.1 | 2 | 2 |
| Leu | 6.9 | 7 | 7 |

TABLE I-continued

Amino acid composition
The amino acid composition of ASP determined as
described above and was compared to published
compositions of C3a and C3a-desArg (Laemmli, U.K.
1970, Nature 227:680–685).

| Amino Acid | ASP | C3a* | C3a-desArg* |
|---|---|---|---|
| Tyr | 1.8 | 2 | 2 |
| Phe | 2.9 | 3 | 3 |
| His | 2.2 | 2 | 2 |
| Lys | 7.8 | 7 | 7 |
| Arg | 9.9 | 11 | 10 |

*Amino acid composition of C3a as reported by T Hugli (1975, J. Biol. Chem. 250:8293–8301).

The present invention will be more readily understood by referring to the following examples which are given to illustrate the invention rather than to limit its scope.

EXAMPLE I

The adipsin-acylation stimulating protein system in human adipocytes and the regulation of triacylglycerol synthesis Through their capacity to store fatty acids as triacylglycerol molecules, adipocytes serve a vital physiologic role. This Example presents the first evidence that this process can be modulated in human adipocytes by the adipsin/Acylation Stimulating Protein (ASP) pathway and suggests a novel function for the product of this system, ASP.

The data demonstrate that: 1) ASP stimulates triacylglycerol synthesis within adipocytes and this occurs to a greater extent in differentiating than undifferentiated cells (242%±32% vs. 168%±11% $p<0.01$ respectively at an ASP concentration of 88 ng/mL); 2) when ASP is generated in vitro through incubation of its precursor proteins under appropriate conditions, triacylglycerol synthesis increases to the same extent as when plasma-purified ASP is added to the medium; 3) human adipocytes contain mRNA for the specific serine protease, adipsin and the two precursor proteins, C3 and factor B, required to interact for the production of ASP; and 4) the extent to which cultured differentiating adipocytes produce ASP is proportional to the degree to which they have accumulated triacylglycerol mass during differentiation ($r^2=0.7523$, $p<0.0005$). These findings provide the first evidence for the function of the adipsin-ASP system in human adipocytes which, in turn, may enhance our understanding of the processes which regulate triacylglycerol clearance from plasma.

Materials and Methods

Oleic acid [9,10-$^3$H(N)](10.0 Ci/mmol) and D-[1-$^3$H(N)]-glucose (15 Ci/mmol) was obtained from DuPont-New England Nuclear (Mississauga, Canada). Oleic acid (sodium salt), bovine serum albumin-essentially fatty acid free (BSA) were from Sigma (St Louis, Mo.). General chemicals and solvents were from Fisher Scientific (Nepean, Canada). Minimum essential medium (MEM) and Dulbecco's minimum essential medium/F12 (D-MEM/F12), Dulbecco's-phosphate buffered saline (D-PBS) and all other tissue culture supplies were from Gibco (Gaithersburg, Md.). The following reagents for reverse transcriptase/PCR were obtained from the listed suppliers: Moloney Murine Leukemia Virus reverse transcriptase (Gibco BRL, Gaithersburg, Md.), hexanucleotides (Pharmacia LKB Biotechnology Products, Baie d'Urfe, Quebec, Canada), dATP, dCTP, dGTP and dTTP (Boehringer Mannheim, Laval, Quebec, Canada), Taq polymerase (ProMega/Fisher Scientific, Nepean, Ontario, Canada).

Culture of human skin fibroblasts and human preadipocytes

Fibroblasts were cultured as previously mentioned. Human adipose tissue was obtained with informed consent at time of elective laparotomy. The adipose tissue was minced, treated with collagenase and the stromal fraction prepared as described by Hauner at al (Hauner et al, 1989, J. Clin. Invest. 84:1663–1670). Preadipocytes were plated out in 24 well culture dishes and cultured in 10% fetal calf serum (preadipocytes) or in differentiation medium (adipocytes) containing 7.5 mg/L insulin, 1 μM dexamethasone, 33 μM biotin, 17 μM pantothenate and 0.2 nM triiodothyronine for an average of 28 days (Hauner et al, 1989, J. Clin. Invest. 84, 1663–1670). Cells were changed to serum-free D-MEM/F12 the day prior to initiation of the experiment.

Measurement of intracellular triacylglycerol synthesis and mass

For experiments, cells were incubated in DMEM/F12 supplemented with D-[1-$^3$H(N)]-glucose (specific activity 2.4 dpm/pmol or [9,10-$^3$H(N)]-oleic acid complexed to BSA in a 5:1 molar ratio as described by Van Harken (Van Harken et al, 1969, J. Biol. Chem. 244:2278–2285) and added to the cells at a final concentration of 100 μM (average specific activity: 100 DPM/pmol). Triacylglycerol synthesis was measured over a 4 hour period as [$^3$H]-oleate incorporation into triacylglycerol. Following incubation, the cells were washed three times with 1 ml ice cold PBS and extracted with two 1 ml volumes of heptane:isopropanol (3:2). Lipid samples were dried in a centrifuge-evaporator (Canberra-Packard, Canada), reconstituted in 100 μl chloroform: methanol (2:1) and resolved by thin layer chromatography (silica gel 150A™, Whatman, England). Plates were developed in hexanes:ether:acetic acid (75:25:1) with reference lipids run concurrently. The lipids were visualized in iodine vapor and the spots corresponding to triolein were scraped into scintillation vials. The radioactivity was counted in 5 ml of scintillation fluid (Cytoscint-ES™, ICN CA) and counted by scintillation (Beckman Model Counter™, Calif.). Triacylglycerol mass was measured as described by Neri and Frings (Neri & Frings, 1973, Clin. Chem. 19:1201–1202) and expressed as μg triacylglycerol per mg soluble cell protein. Cell proteins were solubilized on the dishes by addition of 0.1N NaOH and measured by the method of Bradford (Bradford, 1976, Anal. Biochem. 72:248–254) using a commercial kit (Bio-Rad, Calif.). Data are reported as means of experiments (with all determinations performed in triplicate)±standard deviation. Statistical significance was set at $p=0.05$ and was determined using paired or two mean Student's t-test as indicated in the figure legends and results.

Isolation and Measurement of Plasma and Medium ASP

Acylation Stimulating Protein was partially purified from human plasma as previously described. Complement factors B, C3 and D (Calbiochem, San Diego, Calif.) were incubated as described to generate C3a/ASP in vitro (Janatova et al 1980, Biochem. 19:4471–4478). ASP was measured in the medium of cultured fibroblasts, cultured human preadipocytes (undifferentiated) and adipocytes (differentiating) following a 24 hour incubation of the cells in DMEM/F12 serum free medium. In all cases, ASP was measured in the medium by an RIA kit specific for C3adesArg (Amersham, Oakville, Canada).

mRNA isolation and RT-PCR amplification

Confluent human skin fibroblasts in T150 flasks were extracted with 3 mL of guanidium thiocyanate solution. Mature fat cells released from the collagenase digestion of adipose tissue during the preparation of the stromal adipocyte precursor cells were also extracted in an equal volume of guanidium thiocyanate solution. RNA was isolated as described by Chomczynski and Sacchi (Chomczynski & Sacchi, 1987, Anal. Biochem. 162:156–159) and quantitated by fluorometry. RNA (1 µg) was reverse transcribed (Kandel et al, 1991, Cell 66:1095–1104) and 8% of this product was amplified by polymerase chain reaction. The primers used are described in Table II.

TABLE II

PCR Primer Pairs

| RNA MESSAGE | | PRIMERS | PRODUCT | SIZE |
|---|---|---|---|---|
| GAP | Sn | GGTGAAGGTCGGAGTCAACGGATTTGG | (69–95) | 978 bp |
| | Asn | GGCCATGAGGTCCACCACCCTGTT | (1047–1024) | |
| LPL | Sn | GAGATTTCTCTGTATGGCACC | | 277 bp |
| | Asn | CTGCAAATGAGACACTTTCTC | | |
| Adipsin* | Sn | GTCACCCAAGCAACAAAGTCC | (765–785) | 268 bp |
| | Asn | TCCTGCGTTCAAGTCATCC | (1014–1032) | |
| Factor C3 | Sn | GCTGCTCCTGCTACTAACCCA | (87–107) | 444 bp |
| | Asn | TAGCAGCTTGTGGTTGAC | (531–514) | |
| Factor B* | Sn | GTTGAAGTCAGGGACTAACACC | (8–29) | 548 bp |
| | Asn | CCACAGTGAAACAATGTGC | (537–555) | |

*Primer design based on computer assisted program from cDNA from the indicated references (Kandel et al, 1991).
Sn = sense, Asn = antisense, Product indicates the location of the primer sequences in the published cDNA sequence. Size indicates the amplified PCR fragment size in bp (base pairs).

In house primers were designed using a computer assisted program (Lowe et al, 1990, Nucleic Acids Res. 18:1757–1761) and were obtained through HSC/Pharmacia Biotechnology Service Centre, Department of Clinical Biochemistry, University of Toronto, Toronto, Ontario. The final reaction contained 0.5 units Taq polymerase, 0.2 mM dNTPs and 1 µM of each primer in a final volume of 20 µL amplified on a Perkin Elmer Cetus™ DNA Thermal Cycler (Perkin Elmer Cetus, Norwalk, Conn.). For each of the primer products, cycling controls were run to establish the assay conditions. One cycle consisted of 1 minute at 94° C., 1 minute at 60° C. and 1 minute at 72° C. The product signal for each message was linear up to 37 cycles in mature fat cell RNA where there was greater abundance of the mRNA of interest. GAP was linear up to 29 cycles in mature fat cell RNA and fibroblast RNA. Therefore a standard cycle number was chosen within the linear range to assay all of the samples. Individual conditions were as follows: glyceraldehyde 3-phosphate dehydrogenase ($10^{-5}$M TMAC, 2.0 mM $MgCl_2$, 25 cycles), lipoprotein lipase (2.0 mM $MgCl_2$, 35 cycles), adipsin (2.5 mM $MgCl_2$, 35 cycles), Factor B ($10^{-5}$M TMAC, 2.0 mM $MgCl_2$, 35 cycles) and complement C3 ($10^{-5}$ M TMAC, 2.0 mM $MgCl_2$, 35 cycles) where TMAC is tetra methyl ammonium chloride. Following PCR amplification, samples were separated on a 9% polyacrylamide gel (Laemmli, 1970, Nature 227:680–685) using 0–8% piperazine di-acrylamide as crosslinker with 100 base-pair ladder as reference (Pharmacia LKB Biotechnology Products, Baie d'Urfe, Quebec, Canada). The gel was silver stained (BioRad Silver Stain™ kit, BioRad, Calif.) and scanned by densitometry on a computer assisted LKB Ultroscan XL Laser Densitometer™ (Pharmacia LKB Biotechnology Products, Baie d'Urfe, Quebec, Canada). Each sample was measured in separate experiments at least 2–3 times and the results were averaged.

Results

Figures 5A, 5B:
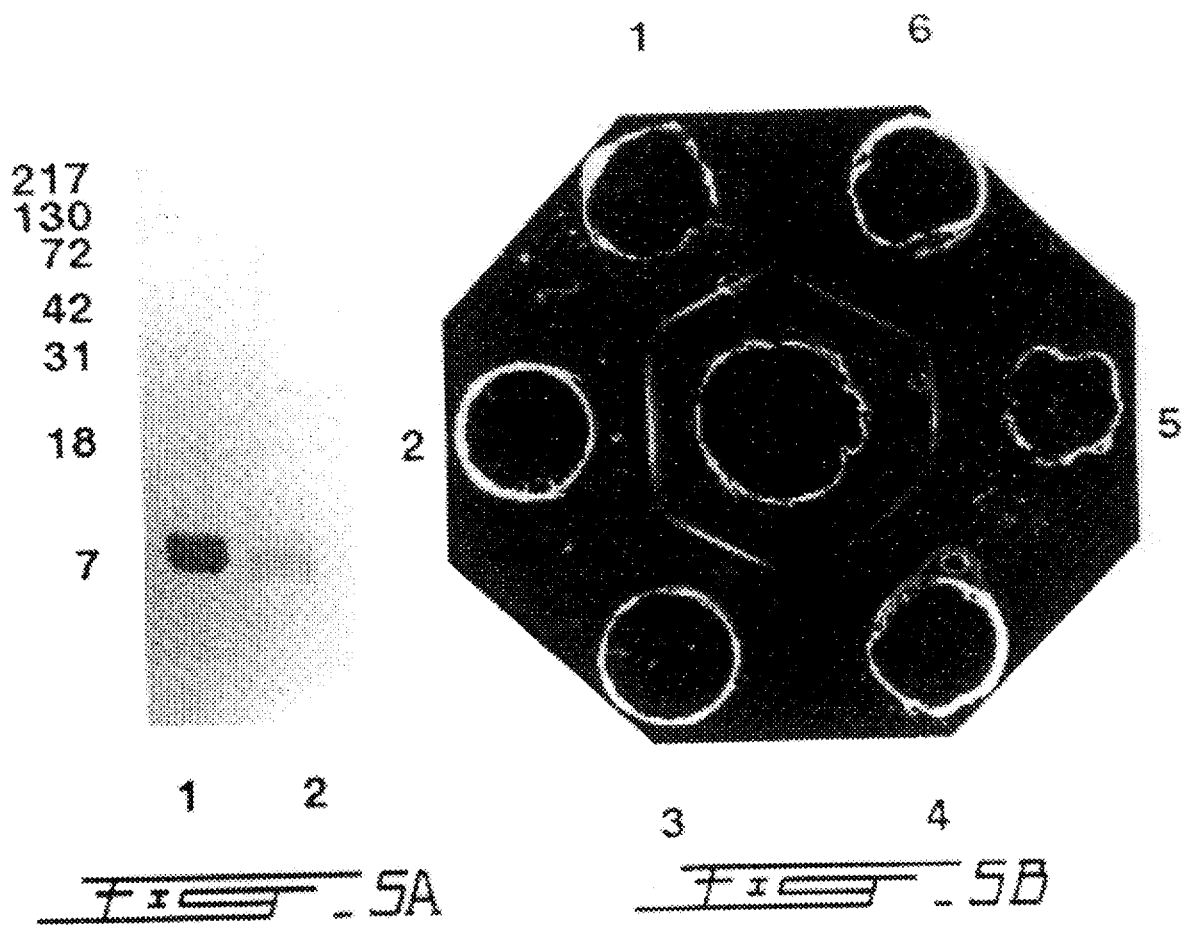
FIG. 5(A–B) is a graph of the ASP stimulation of cultured human differentiating adipocytes.

Human adipose tissue obtained at the time of laparotomy was digested and the cell pellet yielded stromal cells that were cultured to yield differentiating adipocytes. The first question examined Was the effect of ASP on triacylglycerol synthesis in preadipocytes and differentiating adipocytes and these data are shown in FIG. 5. Human preadipocytes were isolated and both preadipocytes and differentiating adipocytes were cultured from each tissue sample. ASP concentration was measured in a partially purified fraction of plasma ASP by RIA. After 24 hours in serum free DMEM/F12 differentiating adipocytes and preadipocytes were changed to serum free DMEM/F12 supplemented with 100 µM $^3$H-oleate complexed to bovine serum albumin and ASP at the indicated concentrations. Triacylglycerol synthesis was measured over a 4 hour period as $^3$H-oleate incorporation into triacylglycerol (nmol/mg cell protein±standard deviation, n=7 experiments). In the differentiating adipocytes, triacylglycerol synthesis was linear for at least 24 hours, and 100 µM oleate was within the linear portion of the fatty acid concentration curve (data not shown). Basal triacylglycerol synthetic rates (shown as 100% on the FIG. 5) were 12.8±2.4 and 65.6±9.3 nmol triacylglycerol/mg soluble cell protein/4h±standard deviation in preadipocytes and differentiating adipocytes respectively. *p<0.05, **p<0.01 for % TG in differentiating adipocytes vs. preadipocytes by two mean t-test. ASP/C3a was partially purified from human plasma as described previously (Cianflone et al., 1990, J. Clin. Invest. 85(3):722–730). ASP concentration determined by RIA and added to the cell culture medium in the presence of 100 µM [$^3$H]-oleate. Triacylglycerol synthesis was measured over a 4 hour period as [$^3$H]-oleate incorporation into triacylglycerol. For each of the two cell types, basal triacylglycerol synthesis was taken as 100% and triacylglycerol synthesis was determined over a concentration range of plasma purified ASP which was added to the medium. The results indicate that ASP induced a concentration-dependent increase in triacylglycerol synthesis in both differentiating adipocytes and preadipocytes. Of interest, the percent increase above basal produced by addition of ASP to the medium was significantly greater in the differentiating adipocytes than in the preadipocytes (p<0.05 for each concentration of ASP by two mean t-test; p<0.01 for the highest concentration of ASP). Such an analysis, however, minimizes the absolute effects on triacylglycerol synthesis caused by ASP. For example, the basal triacylglycerol synthetic rate in preadipocytes was 12.8±2.4 nmol triacylglycerol/mg soluble cell protein/4h (mean±standard deviation), whereas it was 65.6±9.3 nmol triacylglycerol/mg soluble cell protein/4h for the differentiating cells. With addition of 88 ng/ml of ASP to the medium, the two absolute rates of synthesis were 20.3±3.0 and 174.0±50.1 nmol triacylglycerol/cell protein/4h respectively (168%±11% p<0.0005 and 242%±32% p<0.025 respectively). With higher concentrations of ASP and longer incubation times (24 hours) the ASP effect saturated in both preadipocytes and differentiating adipocytes although the absolute triacylglycerol synthetic rate in differentiating adipocytes was still much greater (FIG. 5. inset). It is apparent, therefore, that while ASP acts on both undifferentiated and differentiating adipocytes, it is far more potent in the latter and this may be important in terms of ASP function in vivo.

Figure 6:
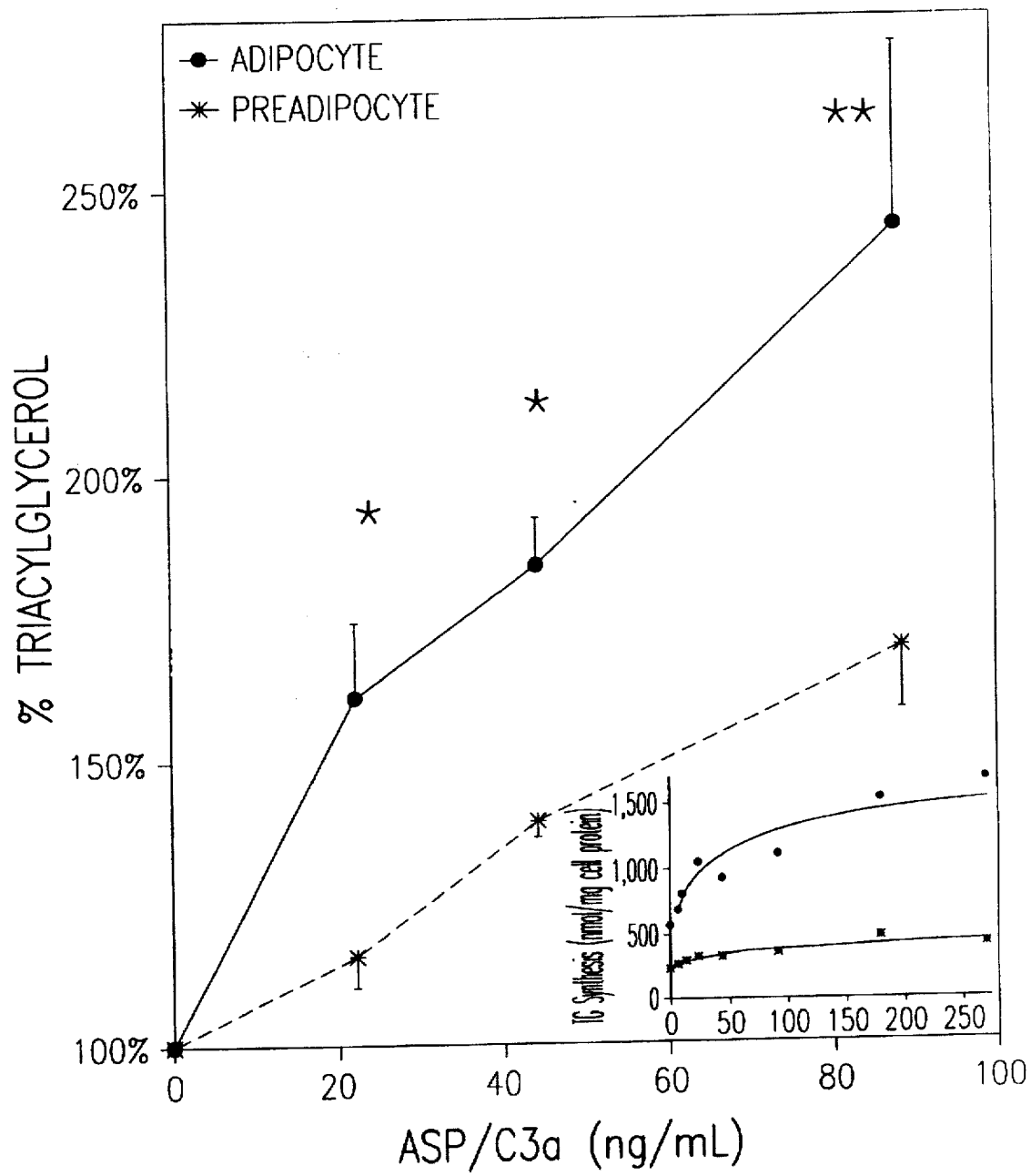
FIG. 6 is the kinetic analysis of ASP effect on triacylglycerol synthesis in preadipocytes and cultured human differentiating adipocytes.

The effect of ASP on apparent Km and Vmax for triacylglycerol synthesis was measured at saturating concentrations of ASP (88 ng/ml) and a representative experiment is shown in FIG. 6. Human preadipocytes and differentiating adipocytes were cultured as described above. ASP concentration was measured in a partially purified fraction of plasma ASP by RIA. After 24 hours in serum free DMEM/F12 differentiating adipocytes and preadipocytes were changed to serum free DMEM/F12 supplemented with ASP (88 ng/ml), $^3$H-glucose (specific activity 2.42 dpm/pmol) and the indicated concentrations of oleate complexed to bovine serum albumin. Triacylglycerol synthesis was measured over a 4 hour period as $^3$H glucose incorporation into triacylglycerol (nmol/mg cell protein); upper panel: preadipocytes with ( ) and without (+) ASP; lower panel: differentiating adipocytes with (o) and without (*) ASP. Reciprocal analysis linear regression was used to calculate Km and Vmax as shown in the inset. panels. In both the preadipocytes (top panel) and differentiating adipocytes (lower panel) there is a clear effect of ASP at all of the concentrations of oleate tested. However both the net increases (note the different y-axis scales) and the percentage increase is much greater in the differentiating adipocytes than the preadipocytes (351%±72% vs. 230%±66%, p<0.005 respectively). Reciprocal analysis. indicates no change in Km for either the preadipocytes or differentiating adipocytes (15.0 basal vs. 15.8 with ASP for preadipocytes and 4.1 basal vs. 2.6 with ASP for differentiating adipocytes). However there is a large change in Vmax particularly in the differentiating adipocytes: 10.0 basal vs. 20.2 with ASP in preadipocytes and 52.0 basal vs. 181.5 with ASP in differentiating adipocytes. These effects of ASP on cellular Vmax, suggesting enhanced triacylglycerol synthesis capacity, are consistent with the previous results of ASP effect on human skin fibroblast triacylglycerol synthesis although clearly these results are far more pronounced.

Figure 7:
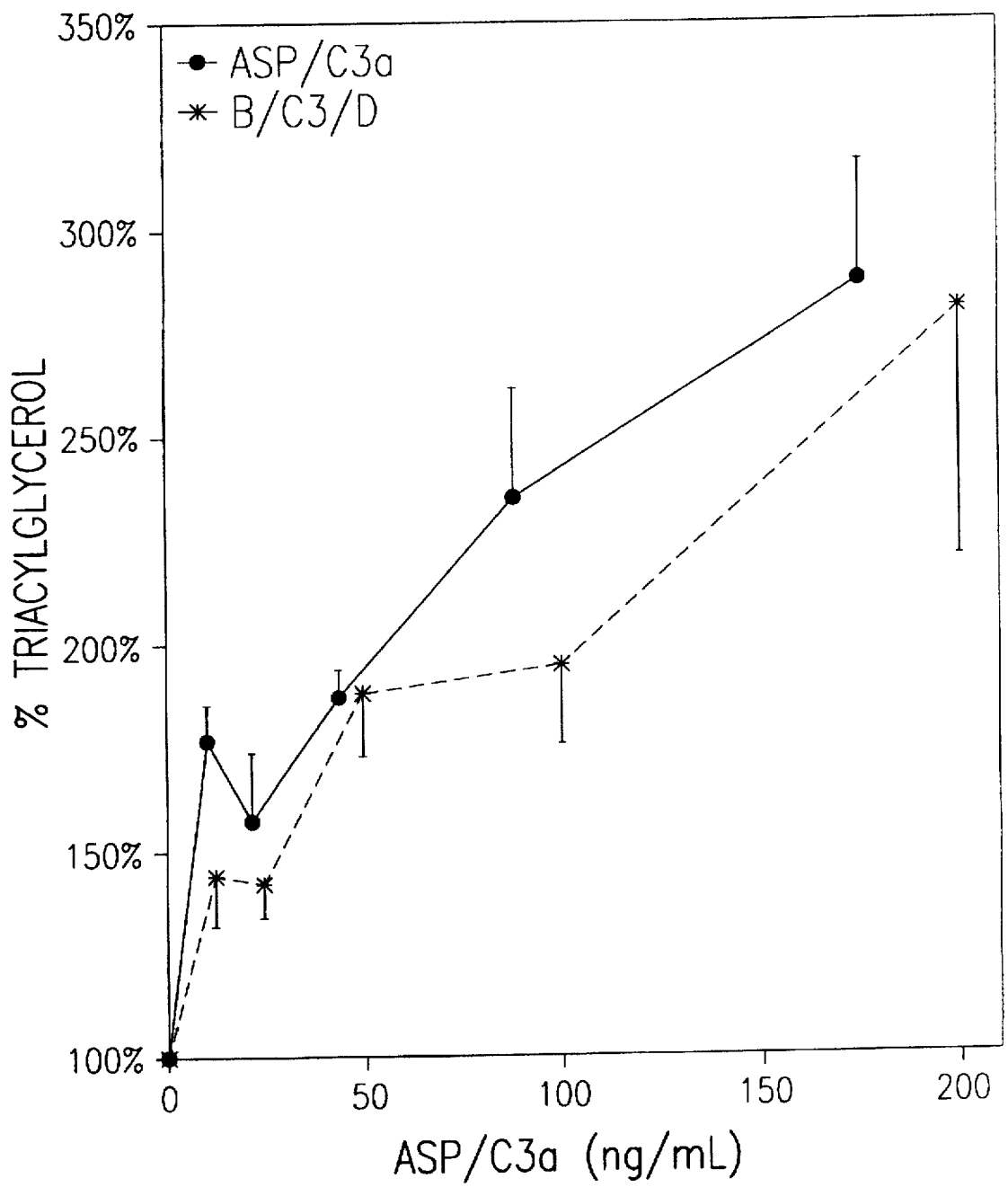
FIG. 7 is a graph of the generation of ASP by factors B, C3 and D.

It was shown previously that ASP can be generated by incubation of factors B, C3, and D (Baldo et al., 1993, J. Clin. Invest. 92(3):1543–1557). Accordingly, it was examined whether ASP generated in vitro would be competent to stimulate triacylglycerol synthesis in human adipocytes. As shown in FIG. 7 when the mixture of precursor proteins and specific serine protease is added to cells, it stimulates triacylglycerol synthesis to a degree comparable to that achieved by adding an equivalent amount of plasma purified ASP (p not significant for plasma ASP vs. in vitro generated ASP from B/C3/D, but p<0.025 for all points vs. basal). Human differentiating adipocytes were cultured as described above. Complement factors B, C3 and D (Calbiochem, San Diego, Calif.) were incubated to generate ASP (C3a) in vitro and the concentration measured by RIA. ASP concentration was measured in a partially purified fraction of plasma ASP by RIA and added to the adipocytes at the indicated concentrations in serum free DMEM/F12 supplemented with 100 µM $^3$H-oleate complexed to bovine serum albumin for 4 hours. Triacylglycerol synthesis was measured as described and expressed as nmol/mg cell protein/4h±standard deviation for an average of 6 experiments: p not significant for plasma ASP stimulation vs. in vitro generated ASP stimulation from B/C3/D by two mean t-test, but p<0.0025 for all points vs. basal by paired t-test. In both cases, the amount of ASP added to the cell incubation mixture is determined by RIA.

Then ASP secretion in these cells were examined and the results are shown in FIG. 8. The preadipocyte stromal fraction of collagenase digested human adipose tissue was cultured in 10% fetal calf serum in minimal essential medium or in differentiation medium for an average of 28 days prior to experimentation as described above. Human skin fibroblasts were cultured as previously described and were incubated in 10% fetal calf serum. ASP was measured in the medium of cultured human preadipocytes (undifferentiated n=30 subjects), adipocytes (differentiating n=30 subjects) and human skin fibroblasts (n=4) following a 24 hour incubation in DMEM/F12 serum free medium. Medium ASP was measured by RIA kit specific for C3a (Amersham, Oakville, Canada) and expressed as ng per mg soluble cell protein±standard deviation. * p<0.0005 compared to preadipocytes (two mean t-test). Three types of cells were studied: human skin fibroblasts, human preadipocytes and human differentiating adipocytes. Both human skin fibroblasts and undifferentiated preadipocytes produce small but detectable amounts of ASP in the medium over a 24 hour period. Incubation in differentiation medium did not affect the production of ASP by human skin fibroblasts. Differentiating adipocytes, by contrast, secrete eight-fold more ASP into the medium over the same time period. The differences in ASP secretion between preadipocytes and adipocytes are also clear at shorter incubation times (4 hours and 8 hours-unpublished observations).

Since ASP is generated through the combined action of adipsin, a serine protease, and factor B and C3, it was examined whether human mature fat cells possess mRNA message for these three proteins and compared the findings to human skin fibroblasts which do not produce substantial amounts of ASP in conditioned culture medium. Primers were prepared for adipsin (factor D), factor B, and C3. Human mature fat cells, isolated from the floating layer of the digested human adipose tissue, were extracted and the message levels examined. Care was taken that the cycling number used was within the linear range (i.e. signal to PCR cycle number) even in mature fat cells where there is greater cellular abundance of the particular mRNA of interest. Average results of 8 human skin fibroblast cell lines and mature fat cell preparations from 13 subjects are shown in FIG. 9. RNA was isolated from one T150 flask of human skin fibroblasts or from mature fat cells isolated by collagenase digestion of adipose tissue. 1 µg of RNA was reverse transcribed and amplified by PCR. The following messages were amplified by PCR: GAP (glyceraldehyde-3-phosphate dehydrogenase, 978 bp), LPL (lipoprotein lipase, 277 bp), ADN (adipsin, 268 bp), C3 (complement C3, 444 bp) and B (Factor B, 548 bp). PCR products were separated by gel electrophoresis and silver stained. Gels were scanned and results are expressed in arbitrary densitometric units as average±standard deviation. Results are the average of 8 human skin fibroblast cell lines and mature fat cell preparations from 13 subjects where *p<0.05, p<0.005, and *p<0.0005 by two mean t-test. There was no difference in glyceraldehyde-3-phosphate dehydrogenase (GAP) between human skin fibroblasts and mature fat cells. As would be expected, there was a very strong signal for the message levels of lipoprotein lipase (LPL) in mature fat cells, with little signal apparent in human skin fibroblasts as previously reported. As well, mature fat cells were also shown to have much higher message levels present for adipsin and C3 ($p<0.0005$ and $p<0.005$ respectively) with a trend towards higher factor B message levels as compared to fibreblasts. This is consistent with the increased levels of ASP secreted by cultured differentiating adipocytes shown in FIG. 8.

Figure 10A:
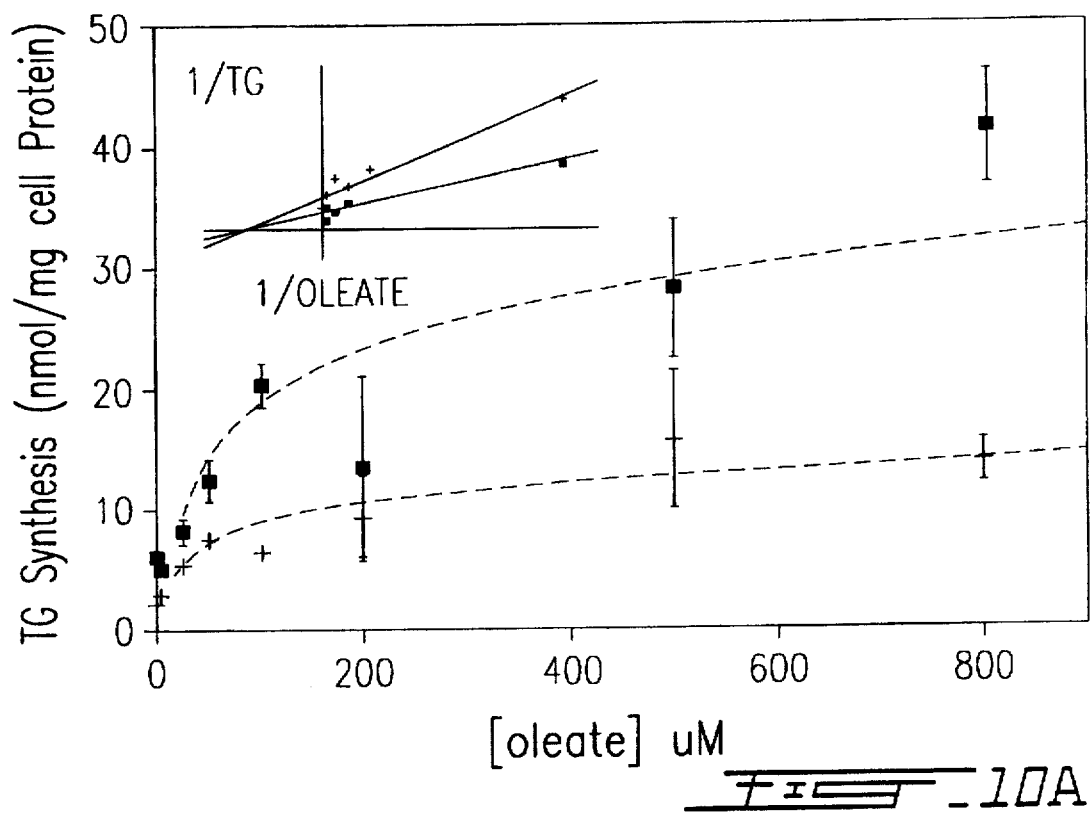
FIG. 10(A–B) shows the correlation of triacylglycerol synthesis to adipocyte differentiation.
Figure 10B:
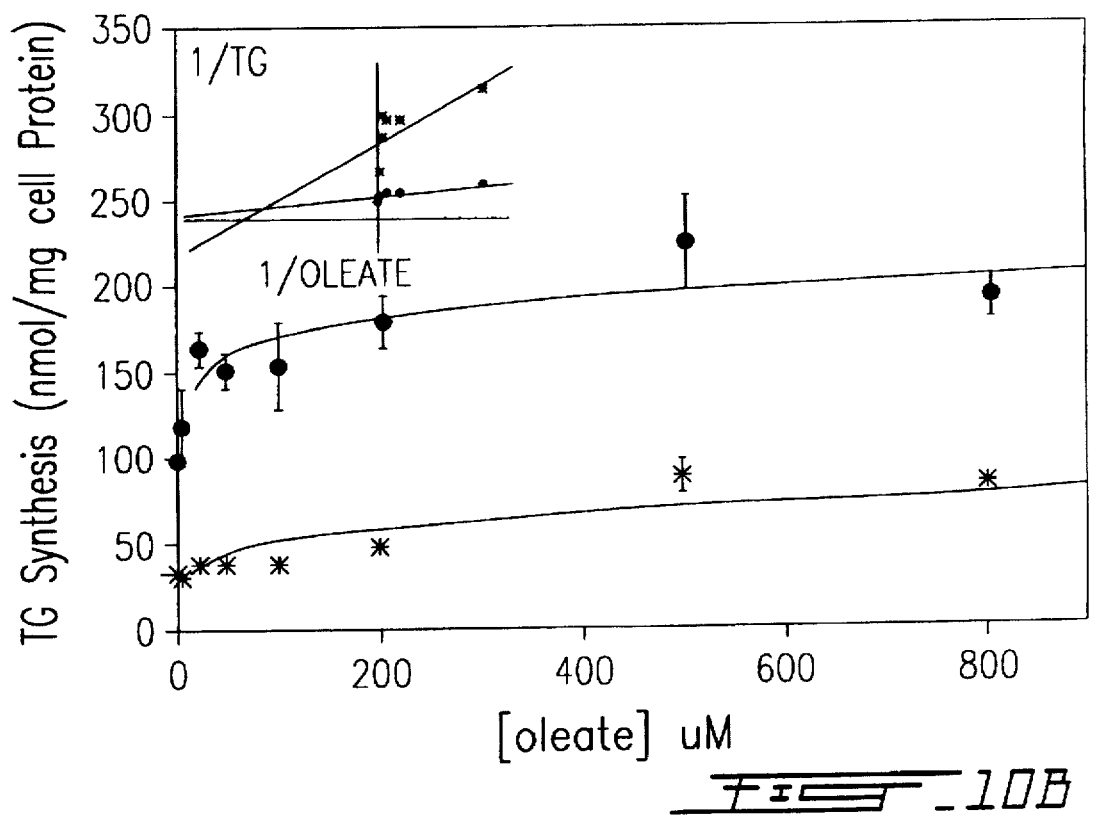

The relation between adipose differentiation, triacylglycerol synthesis and ASP production was then examined in more detail. For this purpose the mass of triacylglycerol per cell protein was taken as an index of differentiation (Hauner et al, 1989, J. Clin. Invest. 84:1663–1670). As shown in FIG. 10, there is a strong positive correlation between changes in triacylglycerol cell mass, which increases as the cell differentiates, and changes in triacylglycerol synthetic rates tested at two different fatty acid concentrations. Cells were cultured as described in Materials and Methods. Following a 24 hour incubation in serum free medium, labelled $^3$H-oleate complexed to bovine serum albumin was added at a concentration of 100 µM (*) or 500 µM (●) for the last 4 hours of the 24 hour incubation time. The cells were extracted and triacylglycerol mass measured and expressed as nmol triacylglycerol per mg soluble cell protein. $^3$H-Oleate incorporation into triacylglycerol is expressed as nmol/ mg soluble cell protein (TG synthesis). Linear regression correlation: 100 µM oleate: $y=0.0349x+34.5$ $r^2=0.3621$, $p<0.0025$; 500 µM oleate: $y=0.499x+91.7$ $r^2=0.545$, $p<0.0025$. The adipocyte becomes larger and triacylglycerol enriched as it differentiates. The triacylglycerol synthetic capacity increases concurrently as well (100 µM oleate: $r^2=0.362$ $p<0.0025$, 500 µM oleate: $r^2=0.545$ $p<0.0025$). The data in FIG. 7 establish that with time during differentiation, adipocytes also acquire an increased capacity to secrete ASP that is proportional to their level of differentiation ($r^2=0.752$, $p<0.0005$). Thus as adipocytes mature, they become increasingly competent to synthesize triacylglycerols and also to secrete ASP.

This Example presents the first evidence of production of ASP and, more importantly, of the potential function of ASP in human adipocytes, where ASP or C3a is the final effector molecule produced by the interaction of factor B, adipsin (or factor D), and complement C3 (Hugli, 1975, J. Biol. Chem. 250:8293–8301). Once generated, ASP facilitates membrane transport of glucose and increases the activity of the final enzyme involved in triacylglycerol synthesis, diacylglycerol acyltransferase, in human fibroblasts and human adipocytes (Yasruel et al, 1991, Lipids 26(7):495–499). A single protein, therefore, is able to stimulate two critical processes involved in the construction of a triacylglycerol molecule.

Such a system might be of considerable physiologic importance. For example, there is now evidence that the rate of triacylglycerol clearance from plasma is not a simple function of the mass of lipoprotein lipase present on the capillary endothelium. Rather, lipoprotein lipase activity seems to be determined by the ambient fatty acid concentration. This, in turn, may be governed by the rate at which triacylglycerol synthesis occurs in adipocytes, thus ensuring that fatty acid concentrations never rise to deleterious levels in the microenvironment. According to this model the action of ASP generated through the adipsin/ASP system may allow upregulation of intracellular triacylglycerol synthesis and thus enhancement of triacylglycerol clearance from plasma (Cianflone et al., 1989, J. Lipid Res. 90(11): 1727–1733; Sniderman et al., 1992, Curr. Opin. Lipidol. 202–207).

On the other hand, dysfunction of this system may be key to the pathogenesis of HyperapoB, a common dyslipoproteinemia in patients with premature coronary artery disease. Adipocytes from patients with this disorder synthesize triacylglycerols less rapidly than adipocytes from normals (Teng et al, 1988, J. Physiol., Pharmacol. 66:239–242) and studies in cultured skin fibroblasts from such patients indicate they respond less well to ASP than do similar cells from normal subjects (Cianflone et al, 1990, J. Clin. Invest. 85(3):722–730). A decreased rate of peripheral fatty acid uptake might result in diversion of these fatty acids to the liver leading, in turn, to an increased rate of secretion of hepatic apoB100 particles. The accumulation of these particles in plasma can then lead to accelerated atherogenesis.

Finally, there is the issue of obesity. Because adipsin message and plasma serum levels were reduced in many murine models of obesity, Spiegelman and his colleagues concluded that downregulation of the system might be a metabolic cause of the obese state (Flier et al, 1987, Science 237:405–408). In humans, in both moderate and severe obesity, plasma ASP levels are elevated as are plasma adipsin levels. Whether the source is adipocytes or some other tissue as well remains to be determined but the observation raises the possibility that the diminished adipsin expression observed by Spiegelman and colleagues (Flier et al, 1987, Science 237:405–408) was an adaptive rather than a causal event.

Clearly much further work is required to test these hypotheses. They are raised now only to indicate that the present findings may be of broad physiologically as well as clinical relevance. For the moment, though, the issue of interest is that human adipocytes appear able to upregulate their capacity to synthesize triacylglycerols by virtue of a complex but nonetheless effective mechanism, the adipsin/ASP pathway. This model will provide, at a minimum, a new framework to understand the processes which regulate triacylglycerol clearance from plasma and disorders which may reflect dysfunction of this pathway such as HyperapoB.

EXAMPLE II

Response of plasma ASP to a prolonged fast and potential implications for the pathogenesis and pathophysiology of obesity Acylation stimulating protein (ASP) is the most potent known stimulant of triglyceride synthesis in human adipocytes. Plasma levels of ASP were measured in 10 age-matched obese patients before and at two week intervals during a 4 week fast compared to values in 16 age matched controls. At baseline, fasting levels of ASP in the obese group were double that in control subjects (116±26 vs. 53±30 nM/L $p<0.001$). During the fast, plasma ASP levels dropped progressively and were within normal range at the end of the fast (63±16 vs. 53±30 nM/L pNS). Protein utilization as evidenced by urine urea nitrogen dropped progressively during the fast, and as plasma ASP levels dropped, there was increasing mobilization of energy from the adipocytes as manifest by increasing plasma free fatty acid and ketone levels. Moreover, when all time points were considered, there was a direct relation between plasma ASP and 24 hour urine urea nitrogen ($r=0.638$ $p<0.001$) indicating that as plasma ASP dropped, energy was mobilized from adipocytes with less utilization of protein for this purpose. The data indicate that understanding the role the adipsin-ASP pathway plays in regulation of the rate of triglyceride synthesis in adipocytes may allow new approaches to the study of the pathogenesis and pathophysiology of the obese state.

Methods

Ten healthy obese subjects (1 man, 9 women) were admitted to the Clinical Investigation Unit of the Royal Victoria Hospital (Montreal, Quebec, Canada). Each had been informed of the nature, purpose, and possible risks of the study which had been approved by the Institutional Human Ethics committee. Upon admission, all subjects were given a weight-maintaining liquid formula diet (Ensure supplemented with Polycose™, Ross Laboratories, Montreal, Canada) for 5 days. Their intake was based on the energy expenditure calculated from the Harris-Benedict equation multiplied by 1.5. They also received a NaCl supplement to ensure a daily intake of at least 120 mmol sodium. After the 5 day baseline period, they underwent a total fast for 4 weeks during which they received potassium and a multivitamin and mineral supplement (Centrum Forte™, Cyanamid Canada, Montreal, Canada). Water intake was at least 1.5 liter per day and coffee, tea or other beverages were not allowed.

Fasting plasma samples were obtained at the end of the baseline period and after week 2 and 4 of the fast and were added to tubes containing aprotinin (Trasylol™, 10,000 kallikrein inhibitor units/ml, FBA Pharmaceuticals, New York, USA). These samples were cooled, centrifuged at 4° C., and aliquots of plasma stored at −20° C. Further samples were added to precooled tubes containing 10% (wt/vol) perchloric acid for ketone body measurement on the deproteinized supernatant. Urine was collected over 24 hour periods and aliquots frozen at −20° C.

Plasma cholesterol, triglycerides and HDL cholesterol and apoB were measured as previously described and plasma free fatty acids by a commercial colorimetric enzymatic method (Boehringer Mannheim, Mannheim, Germany). Plasma ASP levels were determined using an assay validated to measure C3adesarg (Baldo et al., 1993, J. Clin. Invest. 92(3):1543–1557) and urine urea nitrogen was obtained by the autoanalyzer method (Technicon, Tarrytown, N.Y.). Plasma immunoreactive insulin, glucose, and ketones were determined as previously described. All measurements were performed in duplicate.

Values in the obese patients were compared to those in controls by unpaired Student's t test while changes over time within the obese group were analyzed by analysis of variance (ANOVA).

Results

The age, weight, and baseline values for the obese subjects are given in Table III. Values for an age-matched group of control females are shown as well.

TABLE III

Profile of control and obese subjects

| | Control | Obese | P |
|---|---|---|---|
| N | 16 | 10 | |
| AGE (yrs) | 36 ± 10 | 34 ± 11 | NS |
| WEIGHT (kgs) | 59 ± 8 | 103 ± 21 | <0.0005 |
| BMI (kg/m$^2$) | 21.8 ± 2.6 | 37.5 ± 5.8 | <0.0005 |
| CHOL (mM/L) | 4.0 ± 0.9 | 3.6 ± 0.7 | NS |
| TG (mM/L) | 0.79 ± 0.26 | 1.45 ± 0.79 | <0.005 |
| HDL CHOL (mM/L) | 1.62 ± 0.37 | 0.97 ± 0.18 | <0.0005 |
| FFA (µM/L) | 356 ± 148 | 663 ± 136 | <0.0005 |
| ApoB (mg/dL) | 60 ± 16 | 87 ± 26 | <0.0025 |
| ASP (nM/L) | 53 ± 30 | 116 ± 26 | <0.0005 |

Figure 11A:
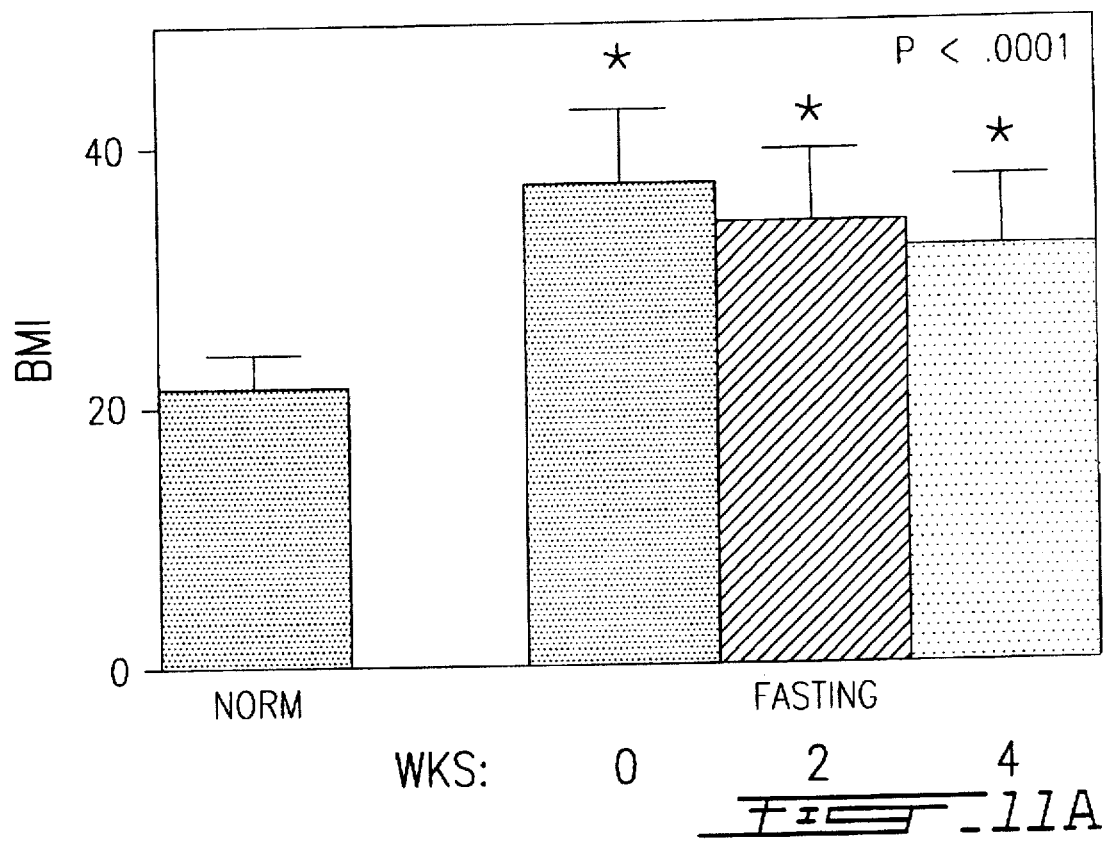
FIG. 11(A–B) shows the sequential changes in plasma triglycerides, HDL cholesterol, plasma total cholesterol and apoB in the obese group during the fast.
Figure 11B:
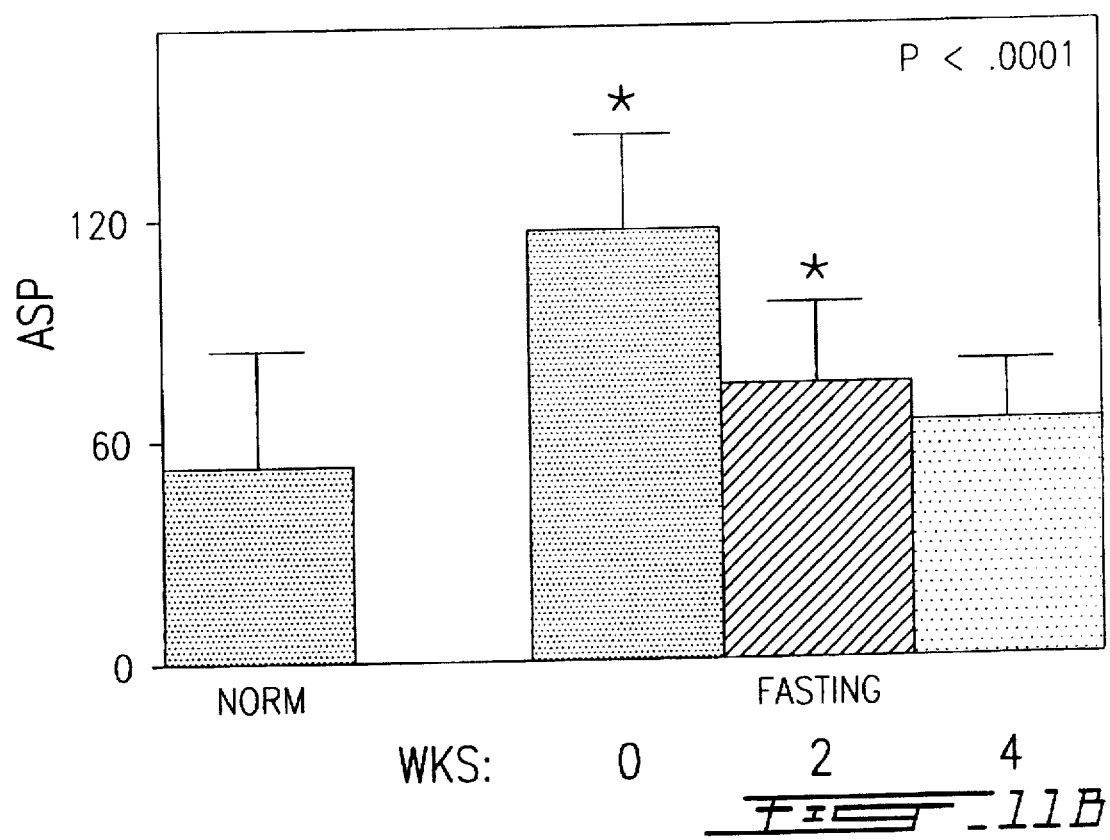
Figure 14:
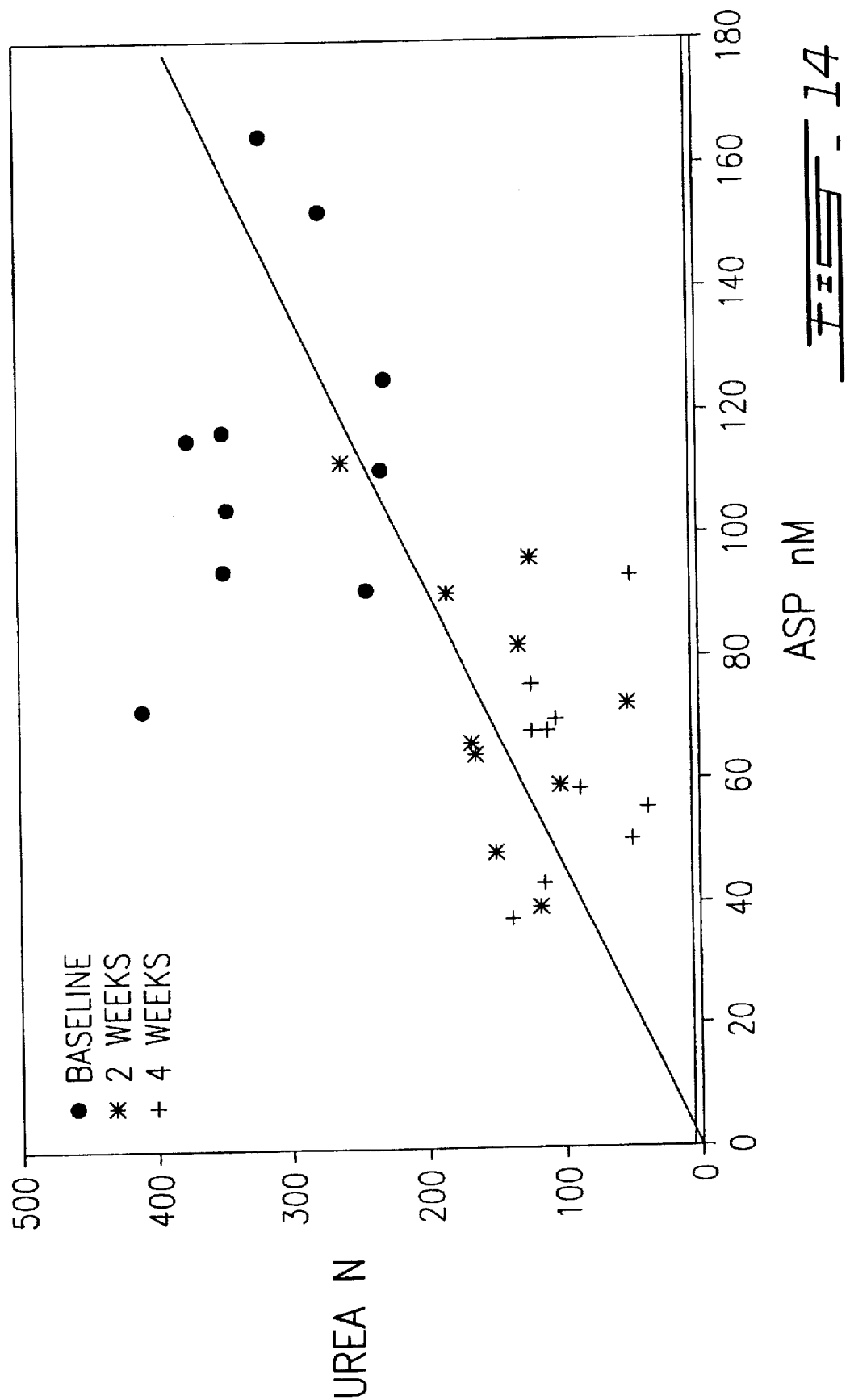
FIG. 14 shows the plasma levels of ASP are plotted against urine urea nitrogen of that day.

CHOL = plasma cholesterol
TG = plasma triglycerides
HDL CHOL = HDL cholesterol
FFA = plasma free fatty acids
ApoB = plasma apolipoprotein B
ASP = acylation stimulating protein The plasma triglyceride and apoB levels are significantly higher and the HDL cholesterol levels significantly lower in the obese compared to the control group but nevertheless remain within the normal range. Plasma free fatty acid and ASP levels, however, are double that in normal. The changes in the plasma lipids, lipoprotein lipids, and apoB over the period of the fast are shown in FIG. 11. Plasma triglycerides were significantly higher than controls only at baseline ($p<0.005$). By ANOVA, there was a significant drop in triglyceride over the study ($p<0.002$). HDL cholesterol was lower than control at all three timepoints ($p<0.0005$) while plasma total cholesterol was significantly less during and at the end of the fast. By ANOVA, there was a significant decrease in plasma total cholesterol over the fast ($p<0.001$). ApoB was higher than control at baseline and at two weeks ($p<0.0025$ and 0.05 respectively). By ANOVA, there was a significant decrease in apoB during the fast ($p<0.03$). All decreased significantly. As shown in FIG. 12, insulin and glucose also decreased significantly during the fast whereas plasma fatty acids rose substantially and plasma ketones rose even more so. The decrease in urine urea nitrogen over the fast was significant ($p<0.0001$) as was the increase in free fatty acids ($p<0.0001$), the increase in ketones ($p<0.0001$) and the decrease in glucose ($p<0.0001$) and insulin ($p<0.006$). Free fatty acids in the obese group were significantly higher than in controls at all timepoints ($p<0.0005$). By contrast, as shown in FIG. 13, as body mass index dropped progressively over the fast, there was a marked decrease in plasma ASP which started at a value more than double that in the controls but decreased to a mean value indistinguishable from that in the controls. BMI decreased significantly during the study ($p<0.0001$) and was significantly higher than in the control group at all time points ($p<0.0005$). ASP decreased significantly over the fast in the obese group ($p<0.0001$). The plasma levels were double that in the controls at baseline ($p<0.0005$) and were still significantly higher at two weeks of the fast ($p<0.05$) but not at 4 weeks (p<NS). The relation between plasma ASP and urine urea nitrogen at all three time points for all patients is shown in FIG. 14. All values for the 10 obese subjects are plotted. There is a direct and significant relation between the two parameters ($r=0.638$, $p<0.001$). There is a direct and statistically significant relation between the two ($r=0.638$, $p<0.001$). That is to say, the higher the plasma ASP, the higher the urine urea nitrogen, and therefore, the greater the apparent protein utilization for energy. Taken together, the data point to increasing utilization of fatty acids but decreasing utilization of protein for energy during the fast.

This Example demonstrates that plasma ASP levels are markedly elevated in obese patients but drop substantially during a prolonged fast. After 4 weeks fasting, plasma ASP levels are no different from normal. During the fast, as plasma ASP dropped, the adipocytes changed from a markedly anabolic to a catabolic status as evidenced by the increase in plasma free fatty acid and ketone levels indicating mobilization of fatty acids from these cells. Furthermore, as plasma ASP dropped, net protein breakdown decreased as well, consistent with the hypothesis that obese patients are at a paradoxical disadvantage with respect to energy mobilization. That is to say, obese individuals should be able to meet all their energy requirements simply by mobilizing fatty acids from their adipocytes. The very elevated plasma ASP levels at baseline would, of course, operate against being able to mobilize energy from adipocytes, and thus necessitate greater mobilization of energy from tissues such as muscle. Increased proteolysis and increased protein turnover per lean body mass have previously been documented in some studies of obese subjects, though the metabolic basis for this has heretofore been obscure.

ASP is identical to C3adesarg. C3adesarg is a terminal product of the interaction of the three proteins which make up the proximal portion of the alternate complement pathway and was thought to be biologically inactive. However, it was shown that ASP is the most potent stimulant yet identified of triglyceride synthesis in human adipocytes (Cianflone et al., 1989, J. Biol. Chem. 264(1):426–430).

Moreover, adipocytes are fully competent to synthesize all the elements of the pathway. Thus, Spiegelman and his colleagues have shown that murine adipocytes contain message for and secrete the three proteins, factor B, factor D (or adipsin) and the third component of complement (C3) necessary to produce ASP (Choy et al., 1992, J. Biol. Chem. 267(18):12736–12741; White et al., 1992, J. Biol. Chem. 267(13):9210–9213).

A recent report of adipsin levels in humans demonstrated that they varied with adipose tissue mass, being higher in the obese and less in those with anorexia nervosa than in the controls. The changes, however, were much less than those that was seen for plasma ASP in this Example, as would be expected given the role of adipsin as an enzyme in the production of ASP.

Whether primary or secondary, however, an elevated plasma ASP in obese subjects due to an increased activity of the adipsin-ASP pathway appears to be metabolically disadvantageous in that it further increases the tendency to sequester energy in the already expanded adipose tissue mass. These patients seem trapped within a vicious cycle: the more obese they are, the more effective they are at storing fatty acids in adipocytes, but the less energy they can mobilize from them, and therefore, the more they must generate from protein. Study of the adipsin-ASP pathway may provide, therefore, new approaches first to the understanding of human obesity and then to its management.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A method of stimulating triglyceride synthesis comprising contacting mammalian cells with pure ASP/C3a-desArg.

2. The method of claim 1 wherein said mammalian cells are human cells.

3. The method of claim 2 wherein pure ASP/C3a-desArg has the amino acid sequence SEQ ID NO: 1
```
Ser Val Gln Leu Thr Glu Lys Arg Met Asx Lys Val Gly Lys Tyr Pro
 1               5                  10                  15
Lys Glu Leu Arg Lys Cys Cys Glu Asp Gly Met Arg Glx Asn Pro Met
            20                  25                  30
Arg Phe Ser Cys Gln Arg Arg Thr Arg Phe Ile Ser Leu Gly Glu Ala
        35                  40                  45
Cys Lys Lys Val Phe Leu Asp Cys Cys Asn Tyr Ile Thr Glu Leu Arg
    50                  55                  60
Arg Gln His Ala Arg Ala Ser His Leu Gly Leu Ala
65                  70                  75
```

4. A method of treating obesity using the method of claim 1.

* * * * *